United States Patent
Koester

(10) Patent No.: US 10,191,005 B2
(45) Date of Patent: *Jan. 29, 2019

(54) ULTRA-COMPACT, PASSIVE, VARACTOR-BASED WIRELESS SENSOR USING QUANTUM CAPACITANCE EFFECT IN GRAPHENE

(71) Applicant: Regents of the University of Minnesota, Minneapolis, MN (US)

(72) Inventor: Steven J. Koester, Edina, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/368,054

(22) Filed: Dec. 2, 2016

(65) Prior Publication Data

US 2017/0082566 A1    Mar. 23, 2017

Related U.S. Application Data

(63) Continuation of application No. 14/111,753, filed as application No. PCT/US2012/033577 on Apr. 13, 2012, now Pat. No. 9,513,244.

(Continued)

(51) Int. Cl.
*H01L 21/20*    (2006.01)
*G01N 27/22*    (2006.01)
(Continued)

(52) U.S. Cl.
CPC ......... *G01N 27/221* (2013.01); *G01N 27/227* (2013.01); *G01R 27/2605* (2013.01);
(Continued)

(58) Field of Classification Search
None
See application file for complete search history.

(56) References Cited

U.S. PATENT DOCUMENTS 9,513,244 B2 * 12/2016 Koester ............... G01N 27/227
2005/0212014 A1    9/2005 Horibe
(Continued)

FOREIGN PATENT DOCUMENTS

WO    20100075012 A3    7/2010
WO    2011023603 A3    3/2011

OTHER PUBLICATIONS

Appenzeller et al., "Toward Nanowire Electronics," IEEE Transactions on Electron Devices, vol. 55, No. 11, Nov. 2008, 21 pp.
(Continued)

*Primary Examiner* — Daniel Whalen
(74) *Attorney, Agent, or Firm* — Shumaker & Sieffert, P.A.

(57) ABSTRACT

An electrical device includes at least one graphene quantum capacitance varactor. In some examples, the graphene quantum capacitance varactor includes an insulator layer, a graphene layer disposed on the insulator layer, a dielectric layer disposed on the graphene layer, a gate electrode formed on the dielectric layer, and at least one contact electrode disposed on the graphene layer and making electrical contact with the graphene layer. In other examples, the graphene quantum capacitance varactor includes an insulator layer, a gate electrode recessed in the insulator layer, a dielectric layer formed on the gate electrode, a graphene layer formed on the dielectric layer, wherein the graphene layer comprises an exposed surface opposite the dielectric layer, and at least one contact electrode formed on the graphene layer and making electrical contact with the graphene layer.

16 Claims, 17 Drawing Sheets

Related U.S. Application Data

(60) Provisional application No. 61/475,539, filed on Apr. 14, 2011.

(51) Int. Cl.
| | | |
|---|---|---|
| *H01L 29/10* | (2006.01) | |
| *H01L 29/16* | (2006.01) | |
| *H01L 29/423* | (2006.01) | |
| *H01L 29/93* | (2006.01) | |
| *H01L 31/08* | (2006.01) | |
| *H01L 31/115* | (2006.01) | |
| *G01R 27/26* | (2006.01) | |

(52) U.S. Cl.
CPC ...... *H01L 29/1025* (2013.01); *H01L 29/1606* (2013.01); *H01L 29/42312* (2013.01); *H01L 29/93* (2013.01); *H01L 31/085* (2013.01); *H01L 31/115* (2013.01)

(56) References Cited

U.S. PATENT DOCUMENTS

| | | |
|---|---|---|
| 2007/0093008 A1 | 4/2007 | Choi |
| 2008/0315277 A1 | 12/2008 | Nakashiba |
| 2010/0025660 A1 | 2/2010 | Jain et al. |
| 2011/0260293 A1 | 10/2011 | Narita |
| 2012/0146743 A1* | 6/2012 | Ermolov ............... B82Y 10/00 333/161 |
| 2012/0161731 A1* | 6/2012 | Voutilainen ............ H02M 3/07 323/273 |
| 2014/0145735 A1 | 5/2014 | Koester |

OTHER PUBLICATIONS

Bolotin et al., "Ultrahigh electron mobility in suspended graphene," Solid State Communications, vol. 146, ScienceDirect, Mar. 6, 2008, 5 pp.
Chen et al., "Intrinsic and extrinsic performance limits of graphene devices on SiO2," Nature Nanotechnology, vol. 3, Apr. 2008, 4 pp.
Chen et al., "Mobility Extraction and Quantum Capacitance Impact in High Performance Graphene Field-effect Transistor Devices," 2008 International Electron Devices Meeting, Technical Digest, Dec. 15-17, 2008, 5 pp.
Dorgan et al., "Mobility and saturation velocity in graphene on SiO2," Applied Physics Letters, vol. 97, No. 8, Aug. 23, 2010, 4 pp.
Dragoman et al., "Graphene-Based Quantum Electronics", Progress in Quantum Electronics 33 (2009), pp. 165-214.
Droscher et al. "Quantum capacitance and density of states of graphene", arXiv:1 001.4690v1 [cond-mal.mes-hall], JARA-FIT and II. Institute of Physics Jan. 26, 2010, 3 pgs.
Fallahazard et al., Dielectric thickness dependence of carrier mobility in graphene with HfO2 top dielectric, Applied Physics Letters, vol. 97, No. 12, Sep. 20, 2010, 4 pp.
Fang et al., "Carrier statistics and quantum capacitance of graphene sheets and ribbons," Applied Physics Letters, 91, No. 9, Aug. 27, 2007, 4 pp.
Farmer et al., "Utilization of a Buffered Dielectric to Achieve High Field-Effect Carrier Mobility in Graphene Transistors," Nano Letters, vol. 9, No. 12, Oct. 19, 2009, 5 pp.
Franklin et al., "Channel and Contact Length Scaling in Carbon Nanotube Transistors," 68th Device Research Conference, Jun. 21-23, 2010, 4 pp.
Han et al., "Energy Band-Gap Engineering of Graphene Nanoribbons," Physical Review Letters, vol. 98, May 16, 2007, 4 pp.
Huang et al., "Nanoelectronic biosensors based on CVD grown graphene," Nanoscale, vol. 2, Apr. 13, 2010, 4 pp.
International Preliminary Report on Patentability from International Application No. PCT/US2012/033577, dated Oct. 15, 2013, 15 pages.
International Search Report and Written Opinion from International Application No. PCT/US2012/033577, dated Aug. 7, 2012, 14 pages.
Kang et al., "An Improved Pregate Cleaning Process for High-k Gate Dielectric Fabrication," Electrochemical and Solid State Letters, vol. 8, No. 11, Sep. 16, 2005, 4 pp.
Kang et al., "Ultrathin HfO2(EOT<0.75 nm) Gate Stack with TaN/HfN Electrodes Fabricated Using a High-Temperature Process," Electrochemical and Solid-State Letters, vol. 8, No. 11, Sep. 12, 2005, 3 pp.
Kim et al., "Realization of a high mobility dual-gated graphene field-effect transistor with Al2O3 dielectric," Applied Physics Letters, vol. 94, No. 6, Feb. 9, 2009, 4 pp.
Knoch et al., "Outperforming the Conventional Scaling Rules in the Quantum-Capacitance Limit," IEEE Electron Device Letters, vol. 29, No. 4, Apr. 2008, 5 pp.
Konar et al., "Effect of high-k gate dielectrics on charge transport in graphene-based field effect transistors," Physical Review B, vol. 82, Sep. 29, 2010, 7 pp.
Lee et al., "RF Performance of Pre-patterned Locally-embedded-Back-Gate Graphene Device," 2010 International Electron Devices Meeting, Technical Digest, Dec. 6-8, 2010, 5 pp.
Li et al., "Large-Area Synthesis of High-Quality and Uniform Graphene Films on Copper Foils," Science, vol. 324, No. 5932, Jun. 5, 2009, 4 pp.
Liang et al., "Performance Projections for Ballistic Graphene Nanoribbon Field-Effect Transistors," IEEE Transactions on Electron Devices, vol. 54, No. 4, Apr. 2007, 8 pp.
Lin et al., "100-GHz Transistors from Wafer-Scale Epitaxial Graphene," Science, vol. 327, No. 5966, Feb. 5, 2010, 2 pp.
Luryi, "Quantum capacitance devices," Applied Physics Letters, vol. 52, No. 6, Feb. 8, 1988, 4 pp.
McCreery et al., "Control of reactivity at carbon electrode surfaces," Colloids and Surfaces A: Physicochemical and Engineering Aspects, vol. 93, Mar. 15, 1994, 10 pp.
Nagashio et al., "Contact resistivity and current flow path at metal/graphene contact," Applied Physics Letters, vol. 97, No. 14, Oct. 4, 2010, 4 pp.
Neto et al., "The electronic properties of graphene," Reviews of Modern Physics, vol. 81, No. 1, Jan. 14, 2009, 55 pp.
Nopper et al., "Wireless Readout of Passive LC Sensors," IEEE Transactions on Instrumentation and Measurement, vol. 59, No. 9, Sep. 2010, 11 pp.
Novoselov et al., "Two-dimensional gas of massless Dirac fermions in graphene," Nature, vol. 438, No. 7064, Nov. 10, 2005, 6 pp.
Ohta et al., "Controlling the Electronic Structure of Bilayer Graphene," Science, vol. 313, No. 5789, Aug. 18, 2006, 6 pp.
Peres et al., "Electronic properties of disordered two-dimensional carbon," Physical Review B, vol. 73, Mar. 16, 2006, 23 pp.
Pinto et al., "p-type doping of graphene with F4-TCNQ," Journal of Physics: Condensed Matter, vol. 21, No. 40, Sep. 14, 2009, 4 pp.
Schedin et al., "Detection of individual gas molecules adsorbed on graphene," Nature Materials, vol. 6, Jul. 29, 2007, 4 pp.
Shan et al., "Direct Electrochemistry of Glucose Oxidase and Biosensing for Glucose Based on Graphene," Analytical Chemistry, vol. 81, No. 6, Mar. 15, 2009, 6 pp.
Son et al., "A Wireless Implantable Passive Microdosimeter for Radiation Oncology," IEEE Transactions on Biomedical Engineering, vol. 55, No. 6, Jun. 2008, 6 pp.
Tang et al., "An enzyme-free quartz crystal microbalance biosensor for sensitive glucose detection in biological fluids based on glucose/dextran displacement approach," Analytica Chimica Acta, vol. 686, Dec. 8, 2010, 6 pp.
Wang et al., "Atomic Layer Deposition of Metal Oxides on Pristine and Functionalized Graphene," Journal of the American Chemical Society, vol. 130, No. 26, Jul. 2, 2008, 3 pp.
Wang et al., "Graphene Frequency Multipliers," IEEE Electron Device Letters, vol. 30, No. 5, May 2009, 5 pp.
Wang et al., "Graphene-Based Ambipolar RF Mixers," IEEE Electron Device Letters, vol. 31, No. 9, Sep. 2010, 5 pp.
Wehling et al., "Molecular Doping of Graphene," Nano Letters, vol. 8, No. 1, Jan. 2008, 6 pp.

(56) References Cited

OTHER PUBLICATIONS

Xia et al., "Measurement of the quantum capacitance of graphene," Nature Nanotechnology, vol. 4, Jul. 5, 2009, 5 pp.
Zhu et al., "Carrier scattering, mobilities, and electrostatic potential in monolayer, bilayer, and trilayer graphene," Physical Review B, vol. 80, Dec. 2, 2009, 8 pp.
Prosecution History from U.S. Appl. No. 14/111,753 dated Oct. 14, 2013 through Oct. 24, 2016, 175 pp.

\* cited by examiner

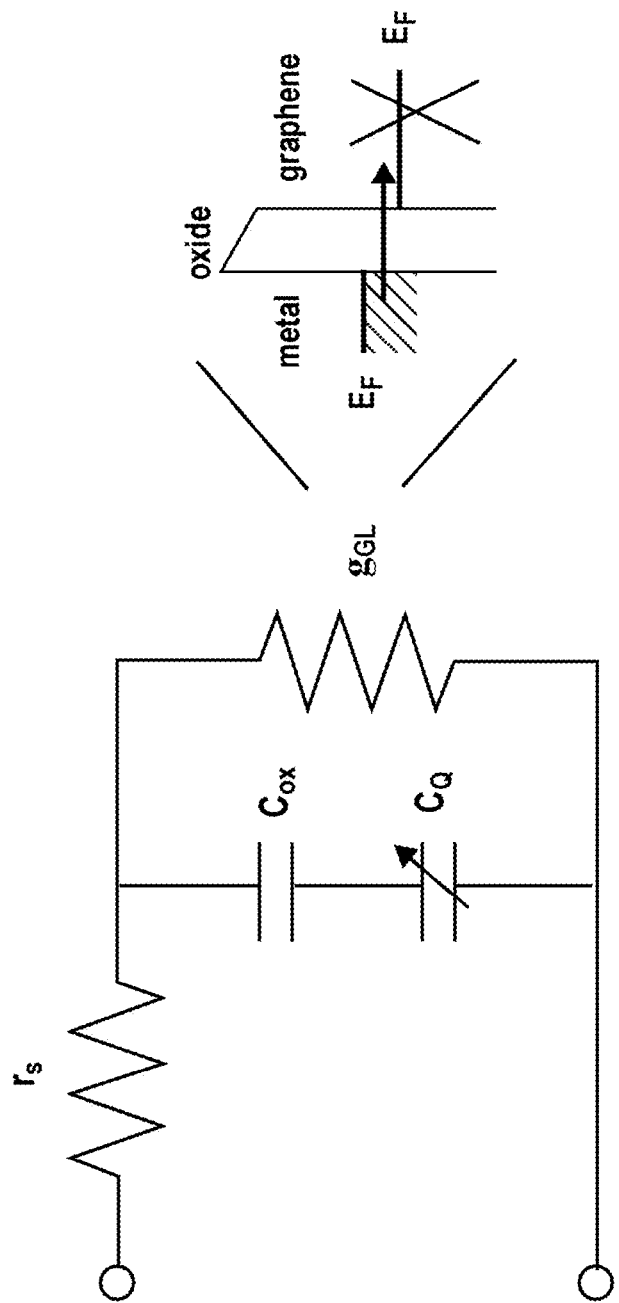

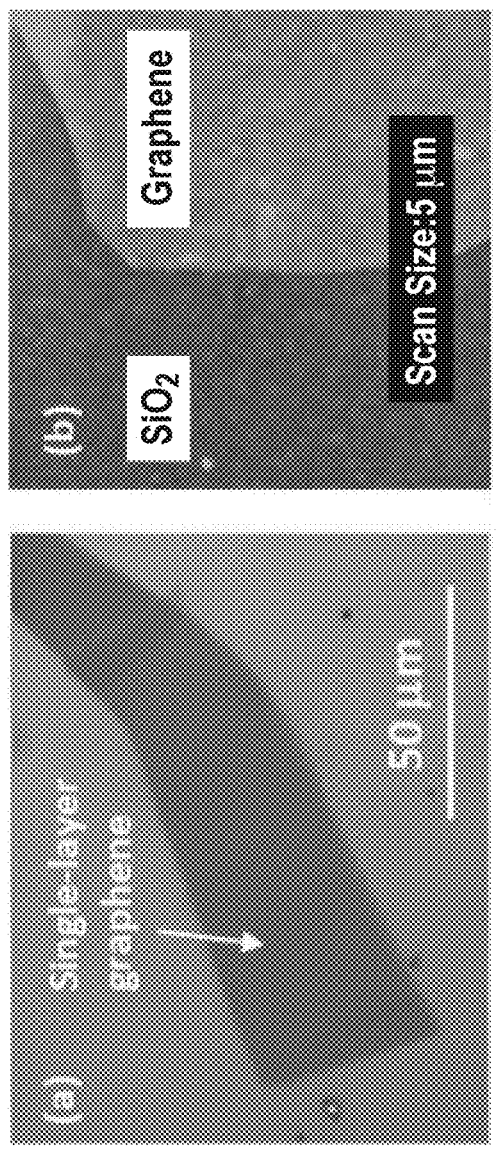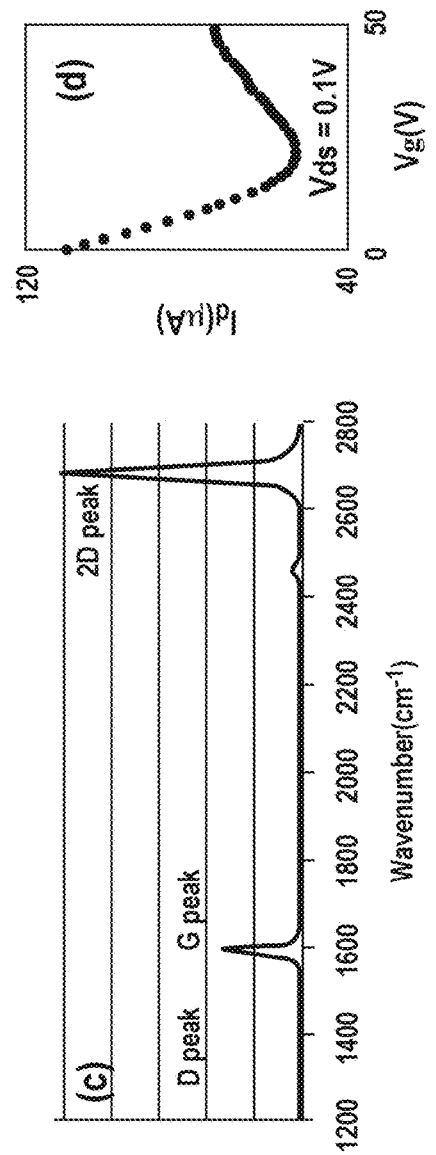
FIGS. 14(a)–14(d)

ULTRA-COMPACT, PASSIVE, VARACTOR-BASED WIRELESS SENSOR USING QUANTUM CAPACITANCE EFFECT IN GRAPHENE

This application is a continuation of U.S. patent application Ser. No. 14/111,753, filed on Oct. 14, 2013, which is a national stage entry under 35 U.S.C. § 371 of PCT Application No. PCT/US2012/033577, filed Apr. 13, 2012, which claims the benefit of U.S. Provisional Application No. 61/475,539, filed on Apr. 14, 2011, the entire contents of each being incorporated herein by reference.

TECHNICAL FIELD

The disclosure relates to electrical devices including sensors.

BACKGROUND

Graphene is a recently isolated two-dimensional form of carbon that has attracted attention in the scientific community due to its unique physical properties. For instance, two-dimensional graphene has zero band gap and a linear dispersion relation near the Dirac point, where the electrons behave like massless Dirac fermions. Graphene has extraordinary transport properties: the Fermi velocity is about $10^8$ centimeters per second (cm/s) and room temperature carrier mobilities over 10,000 centimeters squared per volt-second ($cm^2$/Vs) at a sheet density of $10^{12}$ $cm^{-2}$ have been reported. Carrier mobilities over 200,000 $cm^2$/Vs have also been measured in suspended graphene samples at low temperatures. Graphene also has tremendous mechanical strength and high thermal conductivity. Despite these attractive physical properties, the absence of a band gap has made it difficult to utilize graphene for conventional applications, such as scaled field-effect transistors (FETs) for digital logic. Furthermore, common methods of inducing a band gap in graphene, such as through the formation of nanoribbons or by placing a field across bi-layer graphene, have been shown to degrade the transport properties.

SUMMARY

This disclosure describes electrical devices that utilize the quantum capacitance effect in graphene as a functional basis of the device. The electrical devices take advantage of the relative ease with which graphene can operate in a quantum capacitance limit. The quantum (or degeneracy) capacitance, $C_Q$, is a direct consequence of the Pauli Exclusion Principle, and occurs because Fermions require a Fermi-level shift to increase or decrease their concentration in a material. The quantum capacitance can be expressed as $C_Q = e^2 dn/dE$, where $dn/dE$ is the density of states and e is the electronic charge. Since quantum capacitance is proportional to the density of states, quantum capacitance is lower in materials that have low density of states. Therefore, quantum capacitance effects are most likely to be observable in materials that have low density of states, such as graphene. Evidence of operation in the quantum capacitance regime has been demonstrated in graphene field-effect transistors, and some limited benefits of operation in the quantum capacitance regime have been noted for certain classes of field effect transistors, such as tunneling field-effect transistors (TFETs). However, to date, no compelling device application that utilizes as its principle of operation the quantum capacitance effect in graphene has been proposed.

The techniques described herein utilize the dependence of the density of states in graphene as a function of Fermi-level position (reaching zero at the Dirac point) and the reasonable conductivity of graphene throughout this regime due to its zero band gap and high carrier mobility. This combination of properties, along with the known surface sensitivity of graphene, allows graphene to be used as a charge-sensitive, high-quality-factor (Q) varactor (variable capacitor), a device that could form the basis of a new class of ultra-compact wireless sensors.

As one example, a charge sensitive varactor may be constructed utilizing graphene based upon the quantum capacitance effect. One example device is an extremely compact wireless sensor having uses in a wide range of applications in the commercial, security and medical fields.

In one aspect, the disclosure is directed to an electrical device that includes at least one graphene quantum capacitance varactor.

In another aspect, the disclosure is directed to a wireless sensing system that includes at least one graphene quantum capacitance varactor electrically connected to a first inductor. In accordance with this aspect of the disclosure, the first inductor and the at least one graphene quantum capacitance varactor form an LC oscillator circuit having a resonant frequency responsive to a sense charge collected by the at least one graphene quantum capacitance varactor. The wireless sensing system additionally may include a second inductor electromagnetically coupled to first inductor to produce a signal responsive to a change in the resonant frequency of the LC oscillator circuit.

In a further aspect, the disclosure is directed to a method that includes depositing a graphene layer on an insulator layer, depositing a dielectric layer on the graphene layer, depositing a gate electrode on the dielectric layer, and depositing a contact electrode on the graphene layer.

In an additional aspect, the disclosure is directed to a method that includes etching an insulator layer to define a depression in the insulator layer, forming a gate electrode in the depression, depositing a dielectric layer on the gate electrode, disposing a graphene layer on the dielectric layer, and forming a contact electrode on the graphene layer.

BRIEF DESCRIPTION OF DRAWINGS

FIG. 3(a) illustrates an example buried charge-trapping sensor geometry, FIG. 3(b) illustrates an example surface sensor design with buried gate electrode, and FIG. 3(c) illustrates a top-view layout of an example multi-finger varactor geometry.

FIG. 8(a) illustrates the dependencies on gate oxide thickness, FIG. 8(b) illustrates the dependencies on critical dimension, CD (defined as CD=$L_g$=$L_{ext}$), FIG. 8(c) illustrates the dependencies on mobility, and FIG. 8(d) illustrates the dependencies on contact resistance.

FIG. 12(a) is an example small-circuit equivalent circuit model for a graphene varactor, which shows series resistance ($r_s$), oxide capacitance ($C_{ox}$), quantum capacitance ($C_Q$), and gate shunt conductance ($g_{GL}$).

FIG. 12(b) is a diagram that depicts a gate leakage tunneling mechanism in a graphene varactor.

FIG. 14(a) is a contrast-enhanced optical micrograph of an example of a large piece of exfoliated single-layer graphene.

FIG. 14(b) is an atomic force microscopy (AFM) image of an example single-layer graphene on a silicon oxide ($SiO_2$) substrate.

FIG. 14(c) is a plot of Raman spectroscopy results from an example single-layer graphene piece.

FIG. 14(d) is a plot of an example drain current versus gate voltage ($I_d$-$V_g$) characteristic of an example back-gated graphene field-effect transistor.

DETAILED DESCRIPTION

This disclosure describes electrical devices that utilize the quantum capacitance effect in graphene as a functional basis of the device. In some examples, the electrical device may include wireless sensors, such as a wireless glucose sensor or a wireless radiation sensor.

Figure 1B:
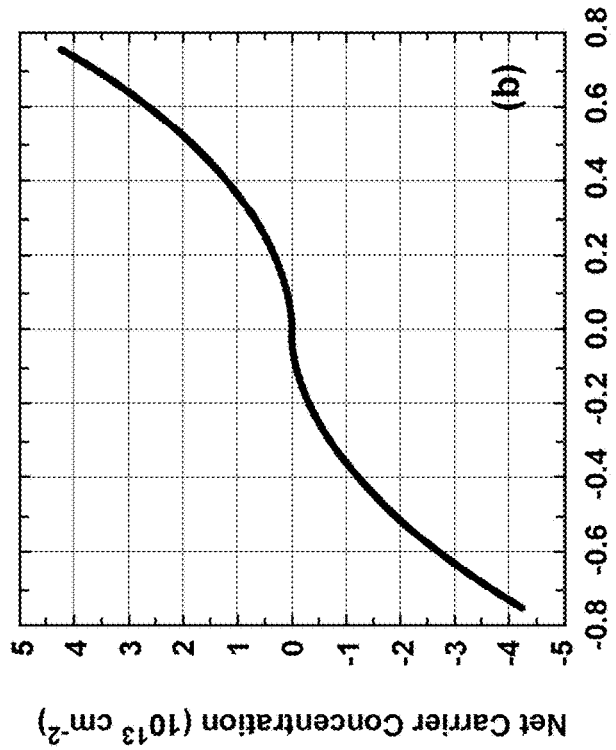
FIGS. 1 (a) and 1(b) are example line diagrams that illustrate, respectively, theoretical total carrier concentration and net carrier concentration in graphene at 300 Kelvin (K) as a function of Fermi energy.
Figure 1A:
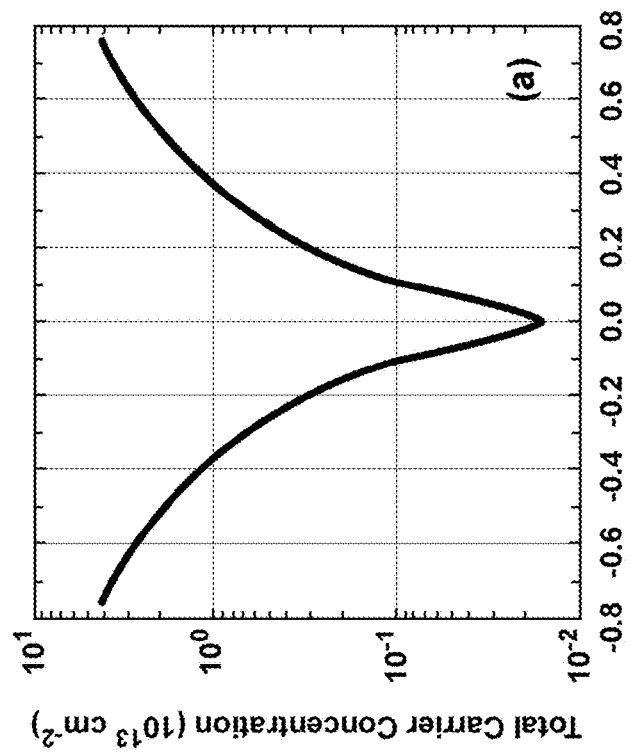

The energy-dependent density of states in graphene, $\rho_{gr}$(E), can be expressed as $$\rho_v(E) = \frac{g_s g_v}{2\pi(\hbar v_p)^2}|E|. \tag{1}$$

where $g_s$ and $g_v$ are the spin and valley degeneracies, respectively, E is the energy relative to the Dirac point, $v_F$ is the Fermi velocity, and $\hbar$ is the reduced Planck's constant. For graphene, $g_s$=2, $g_v$=1 and $v_F$=10 cm/sec. The relation in equation (1) indicates that graphene has a density of states that varies linearly in energy and vanishes at the Dirac point. The carrier concentration can be determined from the density of states by multiplying (1) by the occupation probability and integrating over energy. The electron and hole concentrations, n and p, respectively, can be expressed as:

$$n = \frac{2}{\pi}\left(\frac{kT}{\hbar v_F}\right)^2 \Im(+\eta), \tag{2}$$

$$p = \frac{2}{\pi}\left(\frac{kT}{\hbar v_F}\right)^2 \Im(-\eta), \tag{3}$$

where $$\Im_f(\eta) = \frac{1}{\Gamma(j+1)} \cdot \int_0^\infty \frac{u^j}{1+e^{u-\eta}} \cdot du, \tag{4}$$

k is Boltzmann's constant, T is temperature and $\eta$ is $E_F$/kT, where $E_F$ is the Fermi energy. The two main features of the carrier statistics in graphene are shown in FIGS. 1(a) and 1(b). In FIG. 1(a), the total carrier concentration, $n_{tot}$=n+p is plotted, while the net carrier concentration, $n_{net}$=n-p is shown in FIG. 1(b). FIGS. 1(a) and 1(b) show that even when the net carrier concentration in graphene goes to zero (e.g., at zero Fermi Energy), the total carrier concentration, which determines the conductivity, remains finite.

Figure 2:
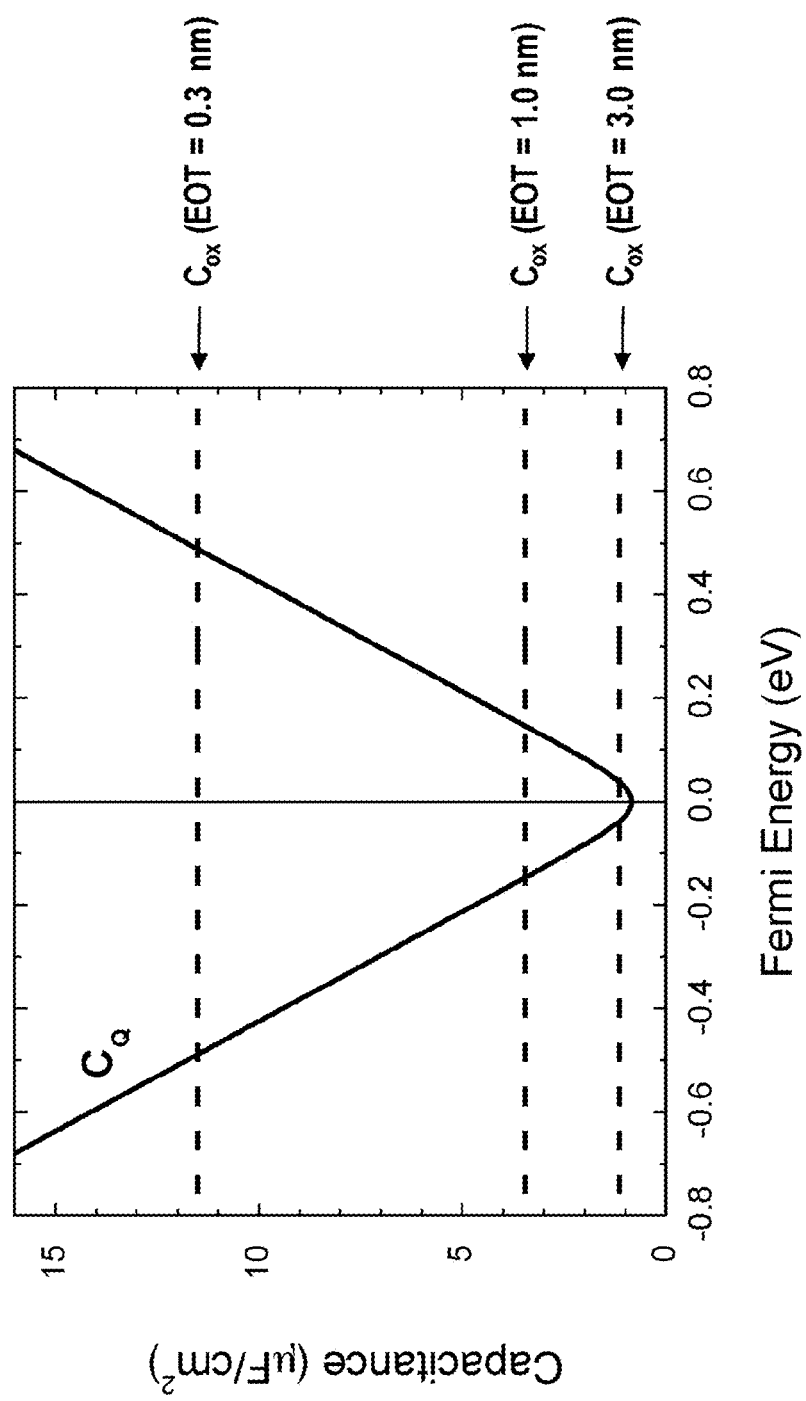
FIG. 2 is an example line diagram that illustrates a plot of theoretical quantum capacitance and oxide capacitance for three different values of effective oxide thickness (EOT) versus Fermi energy at 300 K.

From the relations in (2) and (3), the quantum capacitance, $C_Q$, can be determined as:

$$C_Q = \frac{2e^2 kT}{\pi(\hbar v_F)^2} \cdot \ln\left[2\left(1+\cosh\frac{E_F}{kT}\right)\right], \tag{5}$$

where e is the electronic charge. A plot of $C_Q$ vs. $E_F$ is shown in FIG. 2, where the value of $C_Q$ is compared with values of oxide capacitances for various values of the equivalent oxide thickness (EOT). The plot in FIG. 2 shows that $C_Q$ in graphene can be on the order of the oxide capacitance for some readily achievable values of EOT, 0.3 nm, 1.0 nm, and 3.0 nm. In some examples, the EOT of a varactor may be less than about 5 nm, such as less than about 2 nm, or about 1 nm. Since the total capacitance is determined by the series combination of $C_{ox}$ and $C_Q$, the total capacitance can be modulated by an amount on the order of $C_{ox}/C_{Qmin}$, where $C_{Qmin}$=0.843 pF/cm$^2$ at 300 K. When EOT is less than about 1 nm, this corresponds to capacitance modulation ratios greater than about 4, and these values could be sufficient to allow graphene to be used as a varactor in a wireless readout circuit.

For the quantum capacitance effect to be useful for wireless sensing applications, it is not enough that the capacitance can be varied. The device also has to be able to maintain a high quality factor (Q), so that the varactor can be utilized as part of a resonant LC circuit suitable for wireless readout.

The Q of a capacitor is the reciprocal of the product of its charging delay and the operating frequency (which will ultimately be determined by the size of the inductor in the LC circuit) Q can be expressed as:

$$Q = \frac{1}{2\pi RCf}. \quad (6)$$

Since the magnitude of the capacitance, C, and frequency, f, will be predetermined by the resonant circuit, one practical method to increase Q is to reduce the resistance, R. It is in reducing R where the properties of graphene are suited. The absence of a band gap means that the conductivity of graphene remains reasonably high throughout the entire tuning range. In other words, even when the net charge in the graphene is zero (as shown in FIG. 1(b)), the total number of carriers available for conduction remains finite (as shown in FIG. 1(a), since it consists of a combination of electrons and holes), and such a situation can only occur in a material where band gap energy ($E_g$) is much less than kT (the thermal energy). In graphene, the conductivity drops near the Dirac point (this is the mechanism by which graphene FETs operate), so the remaining channel resistivity is decreased in order to increase the Q.

Figure 3C:
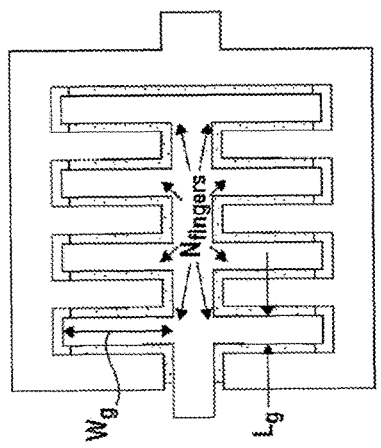
FIGS. 3(a)-3(c) are schematic layouts of example graphene varactor sensor geometries.
Figure 3B:
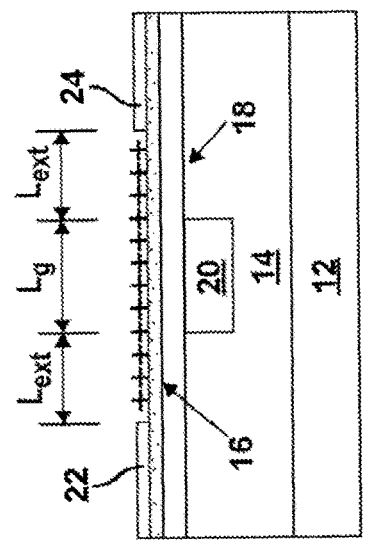
Figure 3A:
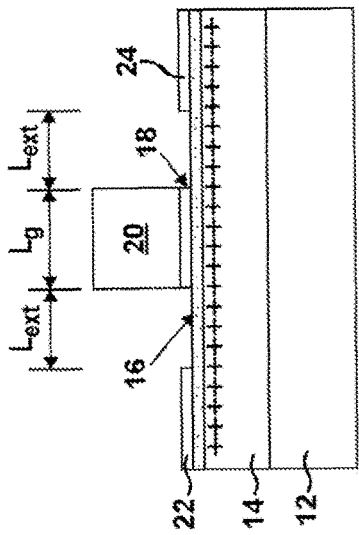

FIGS. 3(a)-3(c) are schematic layouts of example graphene varactor sensor geometries. FIG. 3(a) illustrates an example buried charge-trapping sensor geometry. FIG. 3(b) illustrates an example surface sensor design with a buried gate electrode. FIG. 3(c) illustrates a top-view layout of an example multi-finger varactor geometry.

The example varactor geometry shown in FIG. 3(a) includes a silicon (Si) substrate 12 and an insulator layer 14 formed on silicon substrate 12. In some examples, insulator layer 14 may include, for example, silicon dioxide ($SiO_2$). In other examples, a varactor may not include a silicon substrate 12, and may instead include an insulating substrate, such as quartz, sapphire, or another suitable electrically insulating material. In examples in which the varactor includes an insulating substrate, the varactor may or may not include an insulator layer 14 formed on the insulating substrate.

Graphene layer 16 is disposed on insulator layer 14. In some examples, graphene layer 16 consists of a graphene monolayer. Disposed on graphene layer 16 is a dielectric layer 18, which may be formed of a high-K dielectric material, such as, for example, aluminum oxide ($Al_2O_3$), hafnium dioxide ($HfO_2$), zirconium dioxide ($ZrO_2$), hafnium silicate ($HfSiO_4$), or zirconium silicate ($ZrSiO_4$).

Formed on the dielectric layer 18 is a gate electrode 20. In this way, dielectric layer 18 is disposed between graphene layer 16 and gate electrode 20. Contact electrodes 22 and 24 are also disposed on a surface of graphene layer 16 and make electrical contact with graphene layer 16. As shown in FIG. 3(a), the length of gate electrode 20 is defined as $L_g$, and the distance between gate electrode 20 and first contact electrode 22 or second contact electrode 24 is defined as $L_{ext}$. In some examples, $L_g$ is less than about 5 micrometers (µm), such as between about 50 nanometers (nm) and about 5 µm, or between about 50 nm and about 1 µm, or about 100 nm. In some examples, $L_{ext}$ is less than about 50 µm, such as between about 50 nm and about 5 µm, or between about 50 nm and about 100 nm, or about 100 nm.

FIG. 3(a) shows that the graphene varactor geometry is very similar to that of a field effect transistor, where graphene layer 16 is deposited onto insulator layer 14 and capped with a dielectric layer 18 and gate electrode 20. On either side of gate electrode 20, contacts are made to the graphene, e.g., using contact electrodes 22 and 24. However, unlike a conventional field effect transistor, the "source" and "drain" contact electrodes 22 and 24 are shorted together.

The example design shown in FIG. 3(a) may be suitable for sensing buried charges in the $SiO_2$ layer, and so can have use for applications such as radiation sensing, where ionizing radiation is incident upon the sample and creates trapped positive charges at the buried graphene/$SiO_2$ interface (shown in FIG. 3(a) as positive charges (+)). Such a charge trapping mechanism is utilized in current radiation field-effect transistors (RADFETs), but those devices are not suitable for use in wireless sensors because they cannot be utilized in a varactor geometry.

The example shown in FIG. 3(b) includes a silicon substrate 12 and insulator layer 14. Silicon substrate 12 and insulator layer 14 may include materials similar to those described with respect to FIG. 3(a). In other examples, instead of silicon substrate 12, a varactor may include an insulating substrate, such as quartz, sapphire, or another suitable electrically insulating material. In examples in which the varactor includes an insulating substrate, the varactor may or may not include an insulator layer 14 formed on the insulating substrate.

In contrast to the varactor geometry illustrated in FIG. 3(a), the geometry illustrated in FIG. 3(b) includes a gate electrode 20 recessed into insulator layer 14. For example, gate electrode 20 may be formed by etching a depression in insulator layer 14 and then depositing an electrically conductive material in the depression to form gate electrode 20. Additionally, the varactor geometry in FIG. 3(b) includes a dielectric layer 18 formed on a surface of insulator layer 18 and gate electrode 20. In some examples, dielectric layer 18 may be formed of a high-κ dielectric material, such as, for example, aluminum oxide ($Al_2O_3$) hafnium dioxide ($HfO_2$), zirconium dioxide ($ZrO_2$), hafnium silicate ($HfSiO_4$), or zirconium silicate ($ZrSiO_4$).

Graphene layer 16 is disposed on dielectric layer 18. In some examples, graphene layer 16 consists of a graphene monolayer. Although not shown in FIG. 3(b), a thin protective insulator layer may be formed on graphene layer 16, e.g., on the side of graphene layer 16 opposite to dielectric layer 18. Example materials from which the thin protective insulator layer may be formed include silicon dioxide ($SiO_2$), aluminum oxide ($Al_2O_3$), hafnium oxide ($HfO_2$), or the like.

Contact electrodes 22 and 24 are also disposed on a surface of graphene layer 16. As shown in FIG. 3(b), the length of gate electrode 20 is defined as $L_g$, and the distance between gate electrode 20 and first contact electrode 22 or second contact electrode 24 is defined as $L_{ext}$. In some examples, $L_g$ is less than about 5 µm, such as between about 50 nm and about 5 µm, or between about 50 nm and about 1 µm. In some examples, $L_{ext}$ is less than about 50 µm, such as between about 50 µm and about 50 µm, or between about 50 nm and about 100 nm.

The example design shown in FIG. 3(b) may be suitable for sensing charges on a surface of graphene layer 16, and so can have use for applications such as atmospheric or biological sensing applications. For example, the geometry illustrated in FIG. 3(b) may be used in a glucose sensor. The following analysis is applicable to the configurations shown in both FIGS. 3(a) and 3(b).

In some examples, despite the fact that graphene has a finite conductivity, the channel resistance could be high enough to degrade the Q of the varactor, particularly near the Dirac point. In order to ensure the lowest possible series resistance, a multi-finger varactor geometry such as the one shown in FIG. 3(c) may be used. The multi-finger geometry serves two main purposes. First, it allows the total gate capacitance to be increased while allowing the gate length, $L_g$, to remain small. Maintaining a short gate length may reduce the distance carriers need to travel between the center of the channel and the contacts. Secondly, the multi-finger geometry substantially reduces the resistance associated with the gate fingers, because the fingers are effectively connected in parallel with each other. As shown in FIG. 3(c), in some examples, the geometry of the multi-finger varactor may be defined by the gate width, $W_g$, the gate length, $L_g$, and the number of fingers, $N_{fingers}$.

FIGS. 4(a)-4(d) are conceptual diagrams of an example process of forming a multi-finger varactor as shown in FIG. 3(c). In some examples, the process may include first defining a depression 34 in an insulator layer 32. In some examples, insulator layer 32 includes an $SiO_2$ layer. The $SiO_2$ may be grown on a silicon substrate (not shown in FIG. 4(a)) to any suitable thickness. For example, the $SiO_2$ layer may be up to about 300 nm thick, such as about 90 nm thick. In some instances, the $SiO_2$ layer may be thermally grown on an n-type silicon substrate.

Figure 4A:
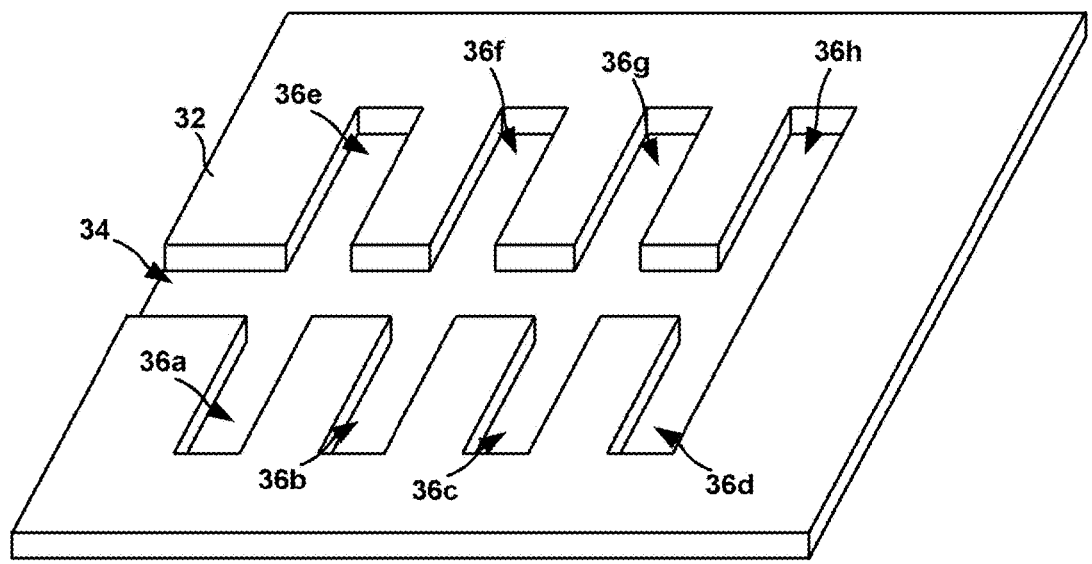
FIGS. 4(a)-4(d) are conceptual diagrams that illustrate an example technique for forming a multi-fingered graphene varactor.

Defining depression 34 may utilize optical contact lithography and buffered oxide etching. The shape of depression 34 may generally correspond to a shape of a gate electrode. For example, depression 34 includes eight fingers 36a-36h. In other examples, depression 34 may include more of fewer fingers, depending on the number of fingers that the gate contact 38 (FIG. 4(b)) is to include. In the example shown in FIG. 4(a), depression 34 defines a shape including four fingers 36a-36d that extend substantially parallel to each other in a first direction and four fingers 36e-36h that extend substantially parallel to each other in a second direction. In the example of FIG. 4(a), the first direction is substantially opposite to the second direction.

Figure 4B:
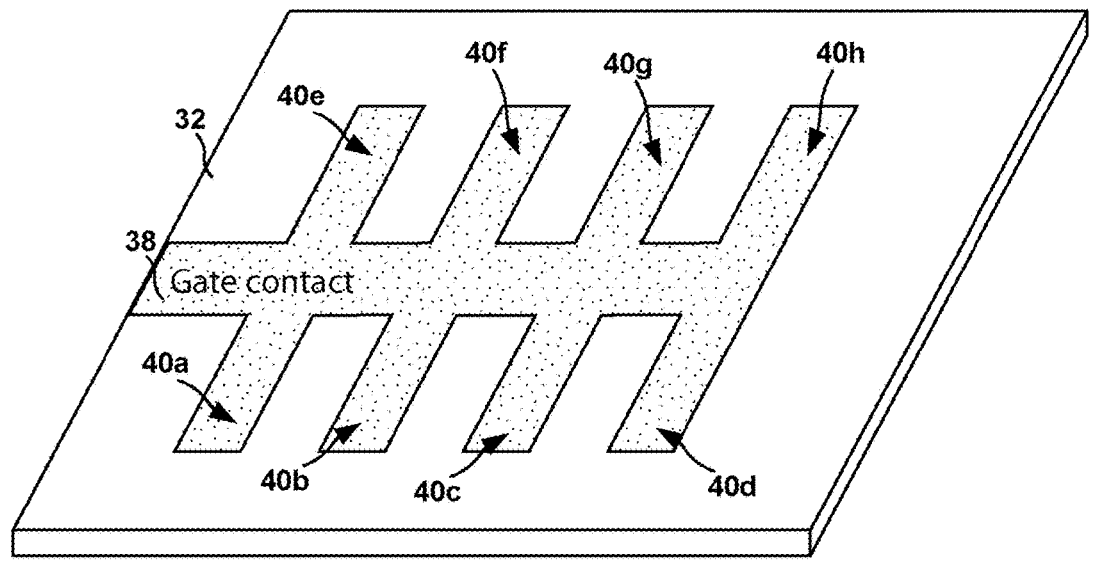

As shown in FIG. 4(b), material is deposited in depression 34 to form gate contact 38 (or gate electrode 38). The material may substantially fill depression 34, e.g., including the eight fingers 36a-36h to form a gate contact 38 with a corresponding number of fingers 40a-40h. The material used to form gate contact 38 may be electrically conductive, such as copper, gold, silver, tungsten, aluminum, titanium, palladium, platinum, iridium, or an alloy including at least one of copper, gold, silver, tungsten, aluminum, titanium, palladium, platinum, iridium, or the like. In some implementations, gate electrode 38 may include a 10 nm layer of titanium and a 50 nm layer of palladium.

In some examples, after depositing the material used to form gate contact 38, a surface of gate contact 38 and insulator layer 32 may be subjected to processing to smooth the surface of gate contact 38 and insulator layer 32 and form a substantially planar surface. For example, chemical mechanical polishing (CMP) may be used to smooth the surfaces. As shown in FIG. 4(b), gate contact 38 includes eight gate electrode fingers 40a-40h. In other examples, gate contact 38 may include fewer than eight gate electrode fingers 40a-40h or more than eight gate electrode fingers 40a-40h. For example, gate contact 38 may include at least two gate electrode fingers.

In some examples, after gate contact 38 has been formed, a dielectric layer (not shown in FIGS. 4(a)-4(d)) may be formed over gate contact 38. For example, a 20 nm layer of hafnium oxide ($HfO_2$) may be deposited on gate contact 38 using atomic-layer deposition (ALD) at about 300° C.

Figure 4C:
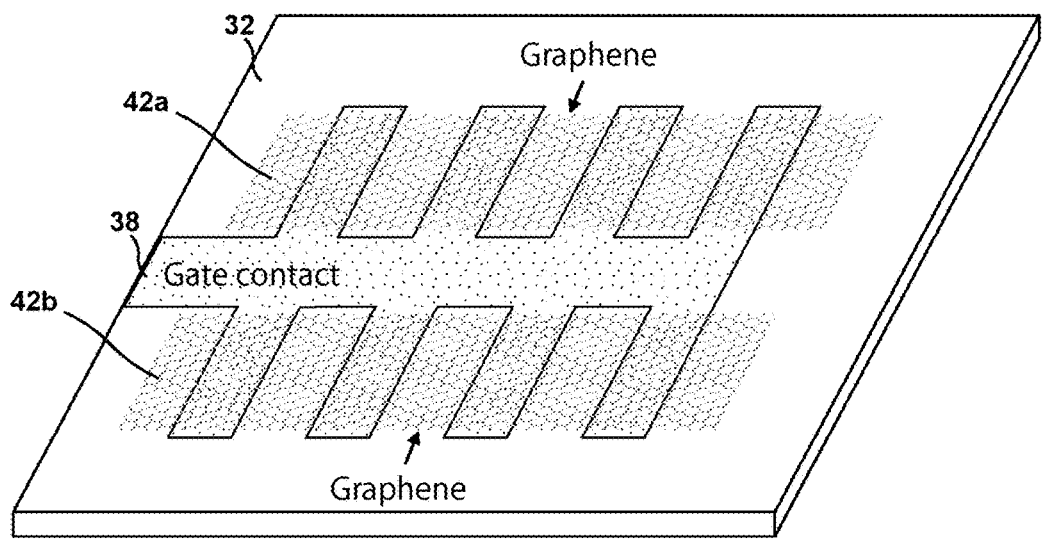

At least one graphene layer 42 may be positioned on gate contact 38 (e.g., over the dielectric layer) and portions of insulator layer 32, as shown in FIG. 4(c). In the example of FIG. 4(c) a first graphene layer 42a is positioned over gate contact fingers 40e-40h (see FIG. 4(b)) and a second graphene layer 42b is positioned over gate contact fingers 40a-40d. In some examples, one or both of first graphene layer 42a and second graphene layer 42b may consist of a graphene monolayer. In other implementations, a single graphene layer 42 or more than two graphene layers 42 may be used in a graphene varactor.

In some examples, the graphene layers 42 are grown using chemical vapor deposition (CVD) on a copper foil. The graphene layers 42 may be coated with poly(methyl methacrylate) (PMMA), and the copper removed using iron(III) chloride ($FeCl_3$). The coated graphene layers 42 are then positioned on gate contact 38 and portions of insulator layer 32 using an aqueous transfer process. The PMMA may be removed using solvent cleaning. In some examples, when graphene layers 42 need to be cut to a different shape, oxygen plasma etching is used to etch the graphene layers 42.

Figure 4D:
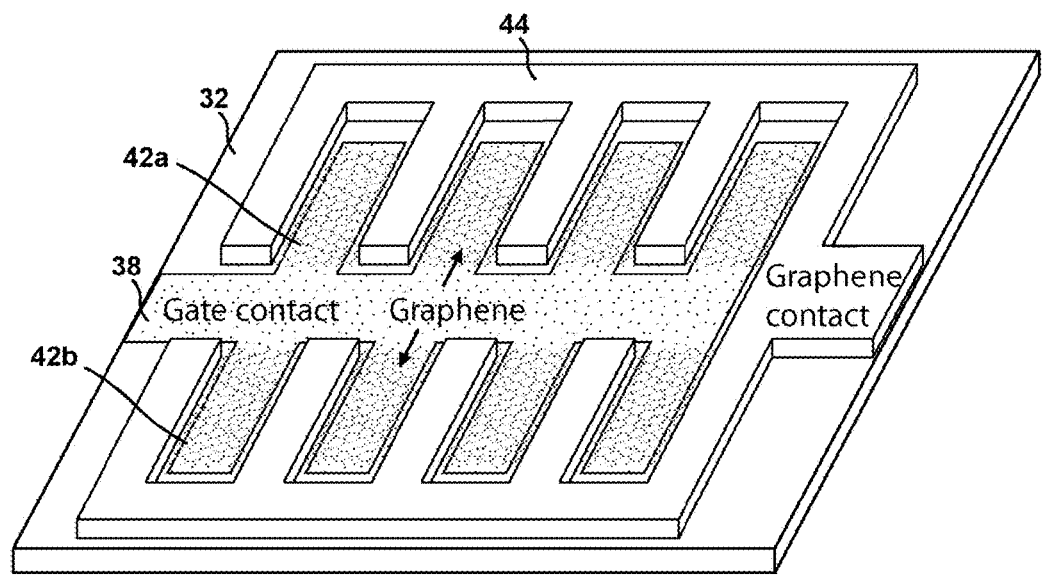

As shown in FIG. 4(d), contact electrode 44 is formed on portions of graphene layers 42 and portions of insulator layer 32. Contact electrode 44 includes electrically conductive material, such as copper, gold, silver, tungsten, aluminum, titanium, palladium, platinum, iridium, or an alloy including at least one of copper, gold, silver, tungsten, aluminum, titanium, palladium, platinum, iridium, or the like. In some examples, contact electrode 44 includes a 10 nm layer of titanium and a 100 nm layer of gold. Contact electrode 44 may be formed using patterning and lifting off processes.

Figure 5:
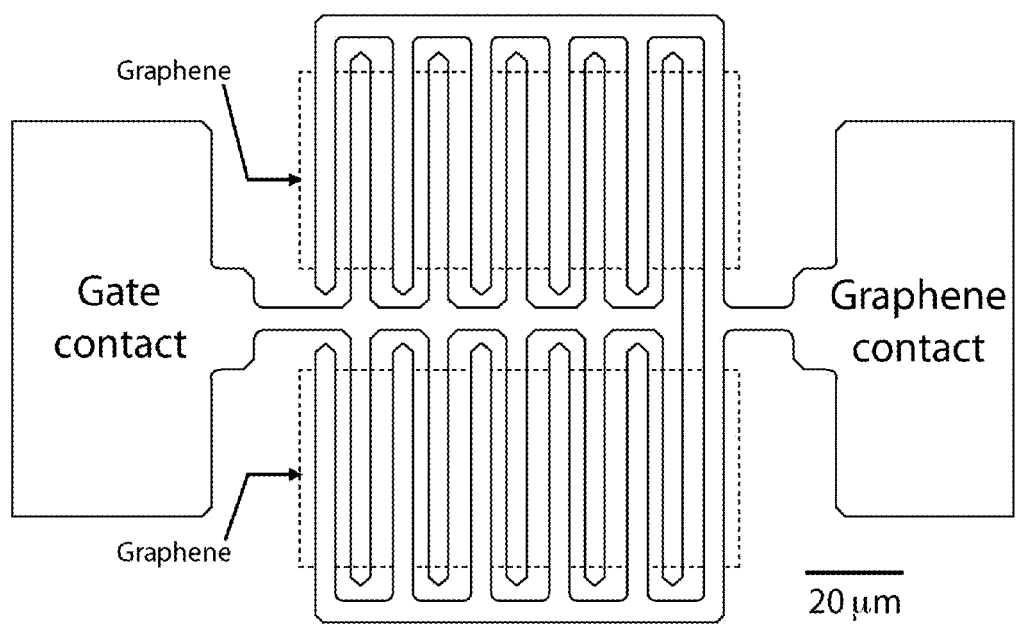
FIG. 5 is an optical micrograph of an example graphene varactor having the geometry shown in FIG. 4(d).

FIG. 5 is an optical micrograph of an example varactor constructed in accordance with the geometry shown in FIG. 4(d). The gate width, $W_g$, of each finger is about 40 μm, and the gate length, $L_g$, of each finger is about 4 μm. The graphene regions have been highlighted for clarity.

Figure 6:
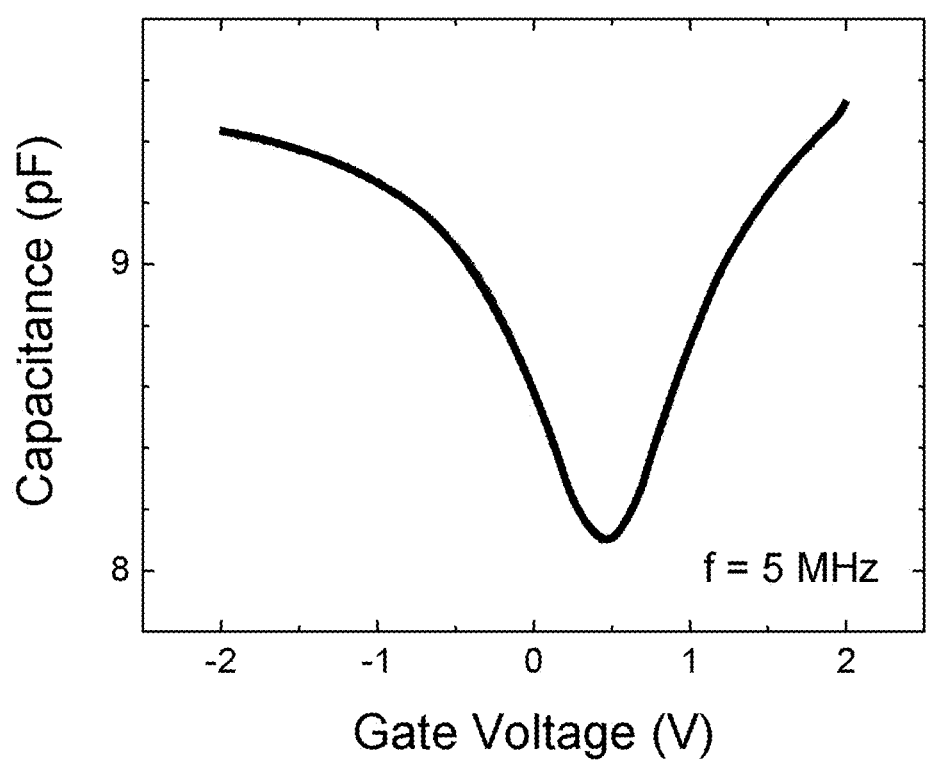
FIG. 6 is a diagram of example experimental results of capacitance versus gate voltage for the example varactor shown in FIG. 5.

FIG. 6 is a diagram of measured results of capacitance versus gate voltage for the example varactor shown in FIG. 5. The characterization of the varactor of FIG. 5 was performed in an open-flow variable-temperature probe station available from LakeShore Cryotonics, Inc., Westerville, Ohio, United States. Before characterization, the sample was baked in vacuum (about $10^{-7}$ Torr base pressure) at about 380° C. for about 30 hours in order to desorb moisture from the graphene surface. Capacitance versus voltage (C-V) measurements were performed using an Agilent B 1500A semiconductor parameter analyzer (available from Agilent Technologies, Santa Clara, Calif., United States) at 5 MHz and using an rms oscillator voltage of 50 mV. No measurable gate leakage was detected in these devices over the range of gate voltages tested. Therefore, the series equivalent circuit mode ($C_s$-$R_s$) was utilized for the C-V measurement. This test shows that the quantum capacitance effect is observable in this device.

The total capacitance, $C_{tot}$, of the sensor design can be modeled as the series combination of the oxide capacitance, $C_{ox}$, and the quantum capacitance, $C_Q$, multiplied by the aggregate gate area:

$$C_{tot} = \frac{C_Q C_{nx}}{C_Q + C_{nx}} \cdot L_g W_g \cdot N_{fingers} \quad (7)$$

where $L_g$ and $W_g$ are the gate length and gate width, respectively, and $N_{fingers}$ is the number of gate fingers. The series resistance, $R_s$, can be modeled as:

$$R_s = \frac{1}{N_{fingers}} \cdot \left[\left(\frac{L_g + L_{ext}}{4W_g}\right) \cdot \left(\frac{1}{e(n\mu_e + p\mu_h)}\right) + \frac{R_c}{W_g}\right]. \quad (8)$$

Here, n and p are the electron and hole concentrations, respectively, while $\mu_e$ and $\mu_h$ are the corresponding electron and hole mobilities. $L_{ext}$ is the extension length as defined in FIG. 3(a), and $R_c$ is the contact resistivity. The gate resistance has been ignored in (8), since for the device dimensions that have been simulated to date, the gate resistance has been negligible relative to the other device resistances. In addition, because carrier mobility depends upon a variety of material and experimental conditions, in these initial simulations, the mobility has been assumed to be independent of carrier density.

Figures 7A, 7B:
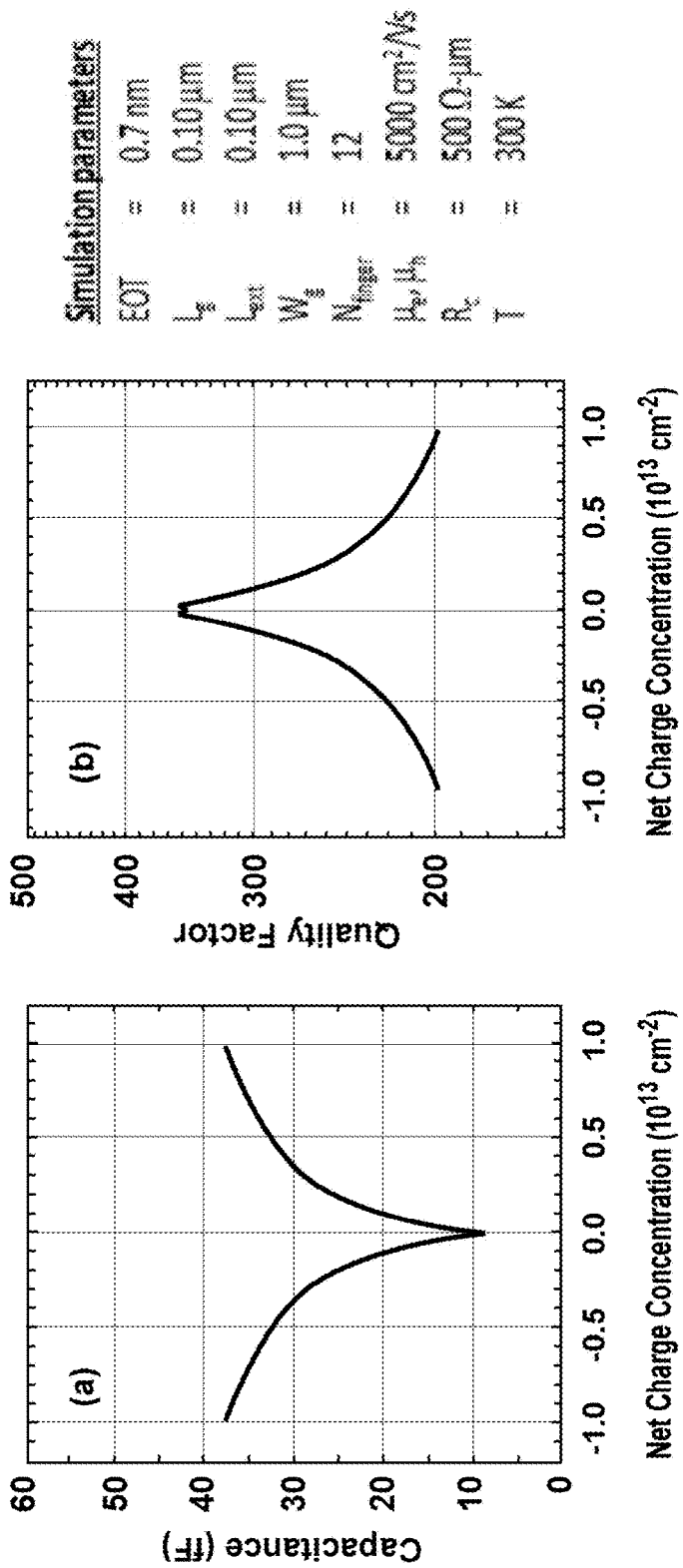
FIGS. 7(a) and 7(b) are example line diagrams that illustrate, respectively, simulated capacitance and quality factor, Q, plotted versus net graphene charge concentration for the device parameters shown on the right.

Simulation results using equations (6-8) are shown in FIGS. 7(a) and 7(b). The simulated parameters are listed on the right side of the figure, and represent realistic material and structural parameters. As expected, the capacitance modulation between $n_{net}=0$ and $n_{net}=10^{13}$ cm$^{-3}$ is greater than a factor of 4, as shown in FIG. 7(a). Additionally, at a frequency of 1 GHz, the Q remains above 200 for nearly the entire modulation range. Note the concentration dependence of Q. The fact that Q decreases with increasing charge concentration is a result of the finite contact resistance, which limits the degree to which R can be decreased as C is increased.

Figures 8A, 8B, 8C, 8D:
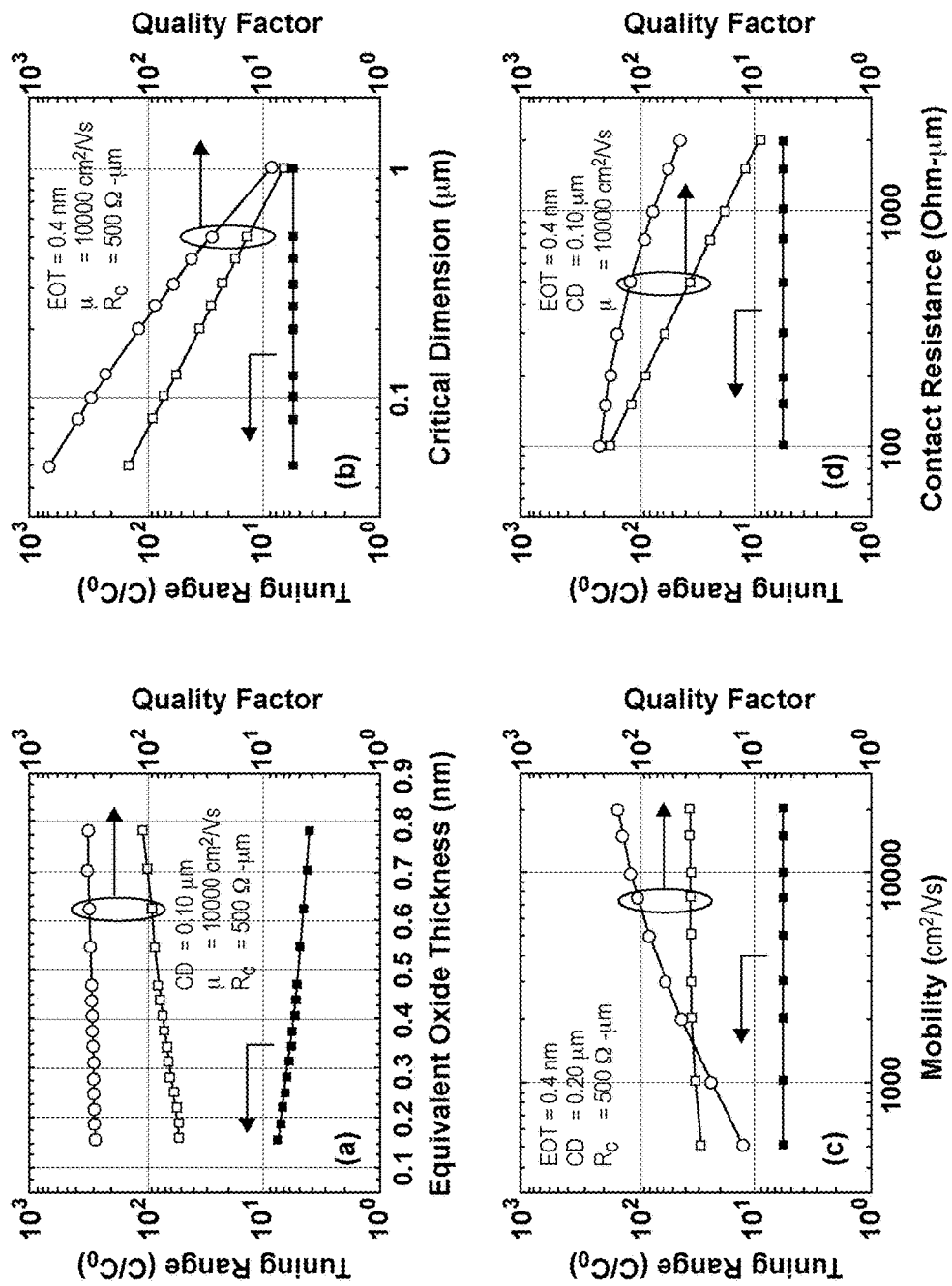
FIGS. 8(a)-8(d) are line diagrams that show variation of the calculated graphene varactor capacitance tuning range (black) and Q (red) at $n_{net}$=0 (solid) and $n_{net}$=$10^{13}$ cm$^{-2}$ (open) as a function of various device parameters.

In order to understand the parameter space better, additional simulations have been performed where a variety of device parameters have been varied, and results shown in FIGS. 8(a)-8(d). FIG. 8(a) shows changes of graphene varactor capacitance tuning range (black line); quality factor, Q, at $n_{net}=0$ (solid red boxes); and quality factor, Q, at $n_{net}=10^{13}$ cm$^{-2}$ (open red circles) as a function of EOT. Here, the simulations show that although the tuning range increases with decreasing EOT, the quality factor decreases somewhat with decreasing EOT. This is because the capacitance increase associated with thinning the gate dielectric is not accompanied by a decrease in the series resistance.

FIG. 8(b) is a diagram that illustrates the dependencies of graphene varactor capacitance tuning range (black line); quality factor, Q, at $n_{net}=0$ (solid red boxes); and quality factor, Q, at $n_{net}=10^{13}$ cm$^{-2}$ (open red circles) on critical dimension, CD (defined as CD=$L_g$=$L_{ext}$). FIG. 8(b) shows that decreasing $L_g$ and $L_{ext}$ allows a high Q to be achieved and that dimensions on the order of about 100 nm may be advantageous. These values are easily achievable using conventional lithographic techniques.

FIG. 8(c) is a diagram that illustrates the dependencies of graphene varactor capacitance tuning range (black line); quality factor, Q, at $n_{net}=0$ (solid red boxes); and quality factor, Q, at $n_{net}=10^{13}$ cm$^{-2}$ (open red circles) on carrier mobility. FIG. 8(d) is a diagram that illustrates the dependencies of graphene varactor capacitance tuning range (black line); quality factor, Q, at $n_{net}=0$ (solid red boxes); and quality factor, Q, at $n_{net}=10^{13}$ cm$^{-2}$ (open red circles) on contact resistivity. FIGS. 8(c) and 8(d) show that carrier mobility has the greatest effect on Q near the Dirac point. At high carrier concentration, the device is substantially insensitive to changes in carrier mobility, since the series resistance is dominated by contact resistance effects. Reducing the contact resistance improves the overall Q and also allows the device to have uniform Q over a wider tuning range, as shown in FIG. 8(d). The tuning range only depends upon EOT, and is invariant to nearly all other device parameters. This likely holds true down to very short gate lengths, due to the very high intrinsic capacitance, which makes the device relatively insensitive to parasitic capacitances.

A second, more detailed simulation was performed to determine the resistance of the varactor. This simulation included the effect of sense charge (external charge accumulated on or near the surface of the graphene) on the carrier concentration in the graphene. Due to the incomplete screening arising from the quantum capacitance effect, a portion of the electric field from the sense charge (depicted in FIG. 1(a) or FIG. 1(b)) terminates on the gate electrode instead of the graphene. This causes the net carrier concentration, $n_{g\text{-}net}$, in the gate region to be lower than in the extension, $n_{ext\text{-}net}$. Here, the net carrier concentration is defined as (n–p). The relations between the sense charge density, $\rho_{sense}$, and $n_{g\text{-}net}$ and $n_{ext\text{-}net}$ can therefore be expressed as follows:

$$n_{g\text{-}net} = \frac{\rho_{sense}}{1 + C_{ex}/C_q}, n_{ext\text{-}net} = \frac{1}{e}*\rho_{sense}, \quad (9)$$

where $\rho_{sense}$ has dimensions of charge per unit area. The channel resistance, $R_{CH}$, includes the resistance of carriers above the gate and in the extensions, and can be expressed as:

$$R_{CH} = \frac{1}{4e\mu W_g N_{fingers}} * \left(\frac{L_g}{n_{g\text{-}tot}} + \frac{2L_{ext}}{n_{ext\text{-}tot}}\right) \quad (10)$$

where $n_{g\text{-}tot}$ and $n_{ext\text{-}tot}$ are the total carrier concentrations (p+n) in the graphene, in the gate and extension regions, respectively. $L_{ext}$ is the extension length as defined as in FIGS. 3(a) and 3(b). To first order, the electron and hole mobilities, $\mu$, can be assumed to be equal, and $\mu$ can further be assumed to be invariant with carrier concentration. The factor of 4 in (10) arises from the varactor symmetry.

Figure 9:
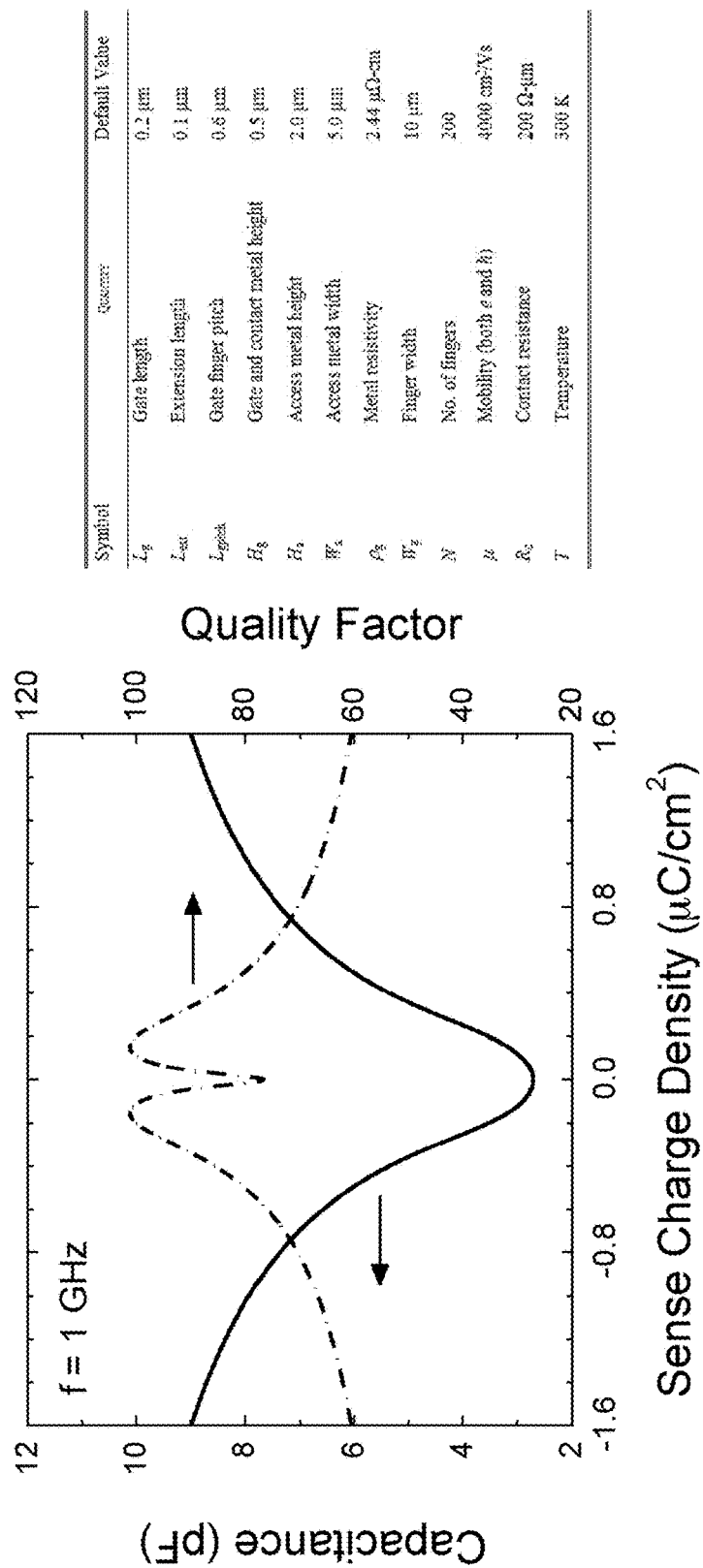
FIG. 9 is a diagram that illustrates capacitance and quality factor as functions of sense charge density for an example multi-finger graphene varactor.

Simulation results using equations (6), (7), (9), and (10), and including additional resistances associated with the gate and contact metallizations, are shown in FIG. 9. The simulated parameters are listed on the right side of FIG. 9, and represent realistic material and structural parameters. The simulations show that capacitance modulation values of roughly 4:1 between $\rho_{sense}=0$ and $\rho_{sense}=1.6$ μC/cm$^2$ can be achieved. Additionally, at f=1 GHz, the Q remains above 60 for nearly the entire modulation range.

The graphene varactor concept offers tremendous potential to reduce the size of a resonant LC circuit compared to MEMS-based sensors. FIG. 10(a) is a line diagram that shows the calculated maximum oscillation frequency of an example LC resonator plotted versus capacitor layout area. FIG. 10(a) includes calculated maximum oscillation frequency versus capacitor layout area data for three different inductance values: 4 nanohenries (nH), 40 nH, and 400 nH. Additionally, FIG. 10(a) includes a data point for a MEMS varactor coupled to an inductor having an inductance of about 11 microhenries (pH). FIG. 10(a) shows that the extremely high capacitance-per-unit-area of the graphene varactor allows resonant frequencies comparable to MEMS based LC circuits, but with much smaller capacitor layout area and much smaller inductors. Since the inductor size is typically much greater than the capacitor, the ability to achieve high capacitances with small layout area is critical to achieving ultra-compact sensors, since it allows the inductor size to shrink without excessively increasing the resonant frequency.

Figure 10B:
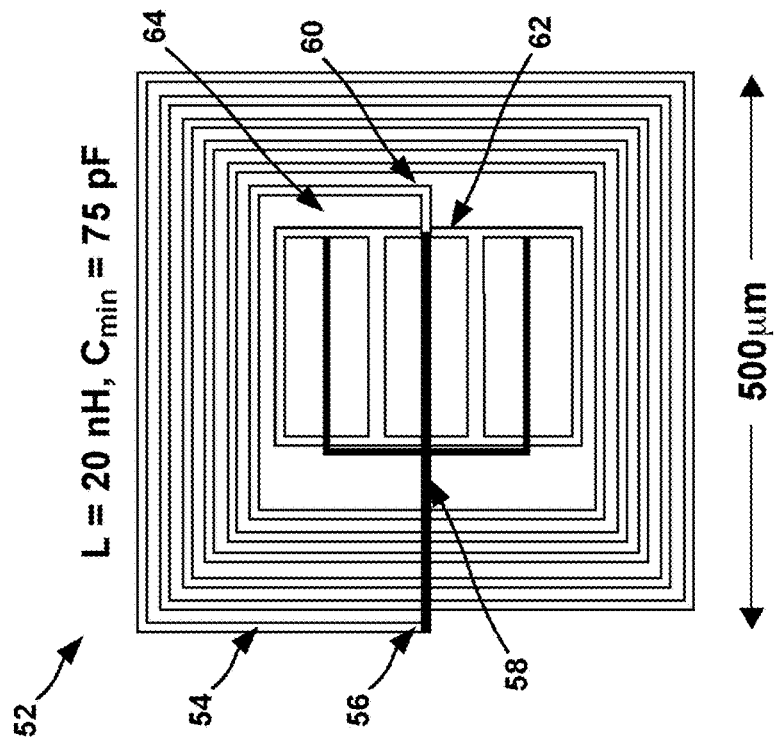
FIG. 10(b) is a conceptual diagram that illustrates an example layout of an integrated graphene varactor and spiral inductor resonator circuit.
Figure 10A:
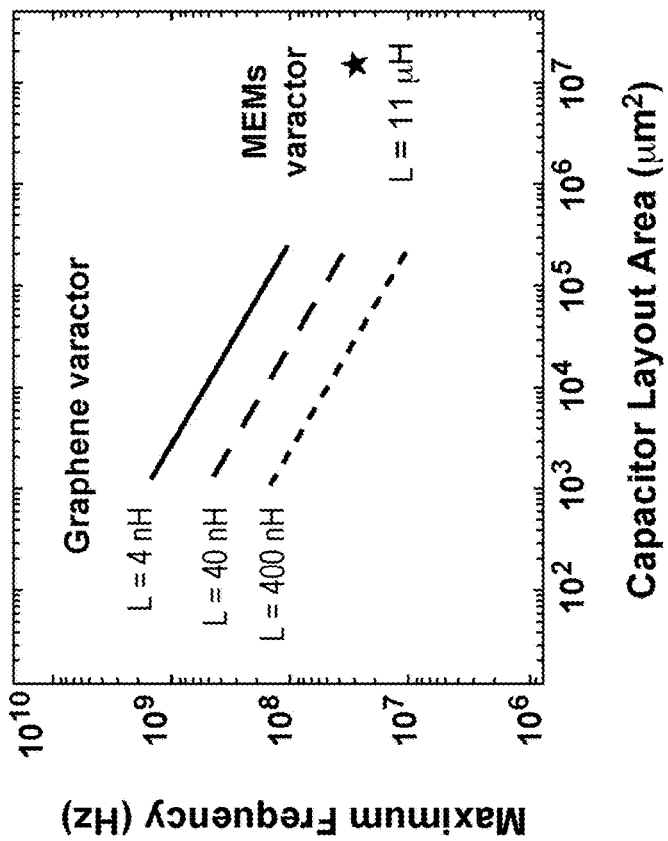
FIG. 10(a) is a line diagram that shows the calculated maximum oscillation frequency of an example LC resonator plotted versus capacitor layout area.

FIG. 10(b) is a conceptual diagram of an example layout for a graphene varactor resonator 52 with integrated on-chip inductor coil 54. This example layout shows that a graphene varactor resonator with maximum frequency of 130 MHz could be realized within a 500 µm by 500 µm footprint. As shown in FIG. 10(b), a first end 56 of the inductor coil 54 is electrically coupled to a gate electrode 58 of the graphene varactor 64 and a second end 60 of the inductor coil 54 is electrically coupled a contact electrode 62 of the graphene varactor 64. The inductor coil 54 shown in FIG. 10(b) has an inductance, L, of 20 nH and the graphene varactor 64 has a minimum capacitance, $C_{min}$, of 75 pF.

Figure 11B:
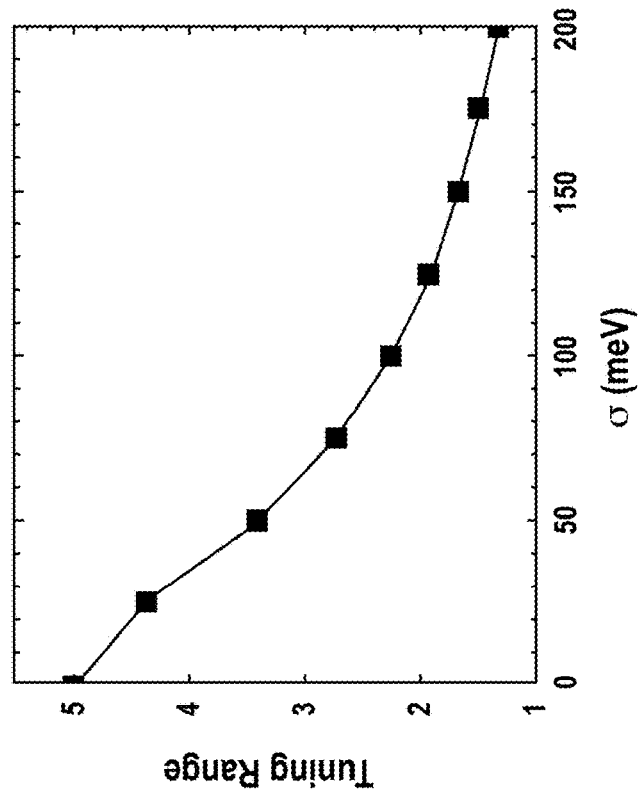
FIG. 11(b) is an example diagram that illustrates tuning range versus values for random potential fluctuations for an example graphene varactor.
Figure 11A:
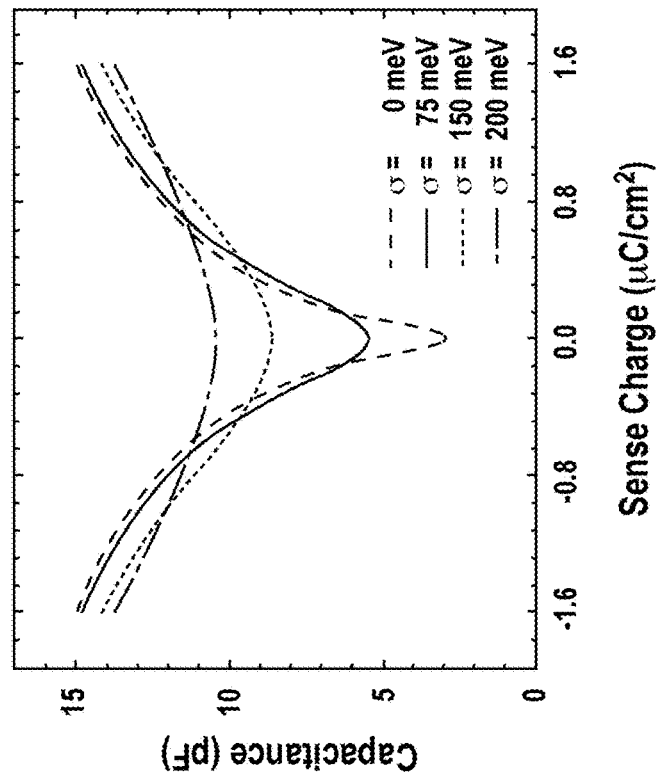
FIG. 11(a) is an example diagram that illustrates capacitance versus sense charge for a graphene varactor using different values for random potential fluctuations.

The disorder in the potential landscape of graphene can cause the Dirac point to be smeared out. However, it is expected that a sufficient tuning range (e.g., greater than about 1.2:1 or, in some examples, greater than about 2:1) can be achieved based on simulations carried out using realistic values for the random potential fluctuations, σ. For example, FIGS. 11(a) and 11(b) show that a tuning range of greater than about 2 may be achieved at random potential fluctuations of less than about 100 mV.

Effect of gate leakage is not likely to have a significant impact on the device operation since the sensors are intended to operate around a dc gate voltage of 0 V, and leakage is only expected to arise due to the small (about 0.1 V) ac voltage that appears across the gate dielectric during sensor operation. This value is significantly lower than the about 0.5 V to about 1 V typically utilized in field effect transistors.

On a silicon substrate with EOT=0.7 nm, hafnium (Hf)-based dielectrics have small-signal conductivity of 0.2 µS/cm$^2$ and 7 µS/cm$^2$ at 0.1 V and 0.5 V, respectively. These values likely would have a minimal impact on Q for the range of parameters investigated in FIGS. 8(a)-8(d). The trends for silicon show that even for conventional Hf-based dielectrics, acceptable leakage is possible even for EOT values as low as 0.5 nm, and further improvements may be possible with higher-κ films.

FIG. 12(a) is an example small-circuit equivalent circuit model for a graphene varactor, which shows series resistance ($r_s$), oxide capacitance ($C_{ox}$), quantum capacitance ($C_Q$), and gate shunt conductance ($g_{GL}$). FIG. 12(b) is a conceptual diagram depicts the gate leakage tunneling mechanism in a graphene varactor.

A process integration scheme for the varactors can be used to achieve proper functionality of the devices. These process issues include how to deposit ultra-thin, low-leakage, high-κ gate oxides on graphene and how to achieve low resistance contacts on graphene.

Referring back to the configurations shown in FIGS. 3(a)-3(c), a back gate electrode can be utilized to modulate a net carrier concentration in graphene. This configuration may be suitable for working with exfoliated graphene, since the graphene does not need to be pre-aligned to the existing features on the substrate. The back gate electrode can also be used to "simulate" the sensing behavior by providing a simple way to modulate the graphene carrier concentration, thus allowing the basic device design issues to be developed. This configuration is an ideal geometry for radiation sensing, and this geometry can be utilized to test the potential of graphene as a radiation-sensitive varactor.

Figures 13A, 13B, 13C, 13D, 13E, 13F:
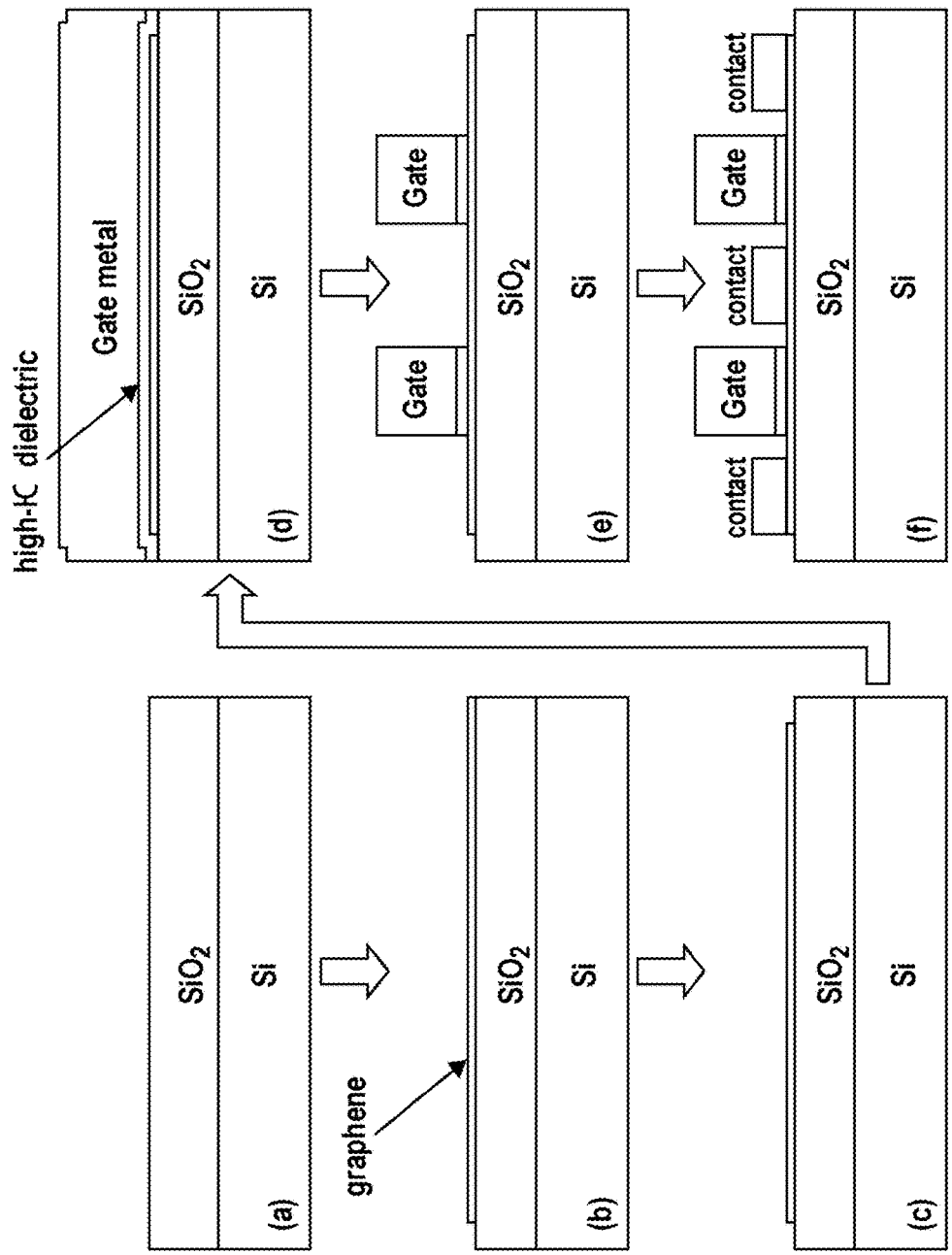
FIGS. 13(a)-13(f) are conceptual diagrams that illustrate an example process flow for forming a graphene varactor having a configuration similar to that shown in FIG. 3(a).

A process flow for forming a graphene varactor having a configuration similar to that shown in FIG. 3(a) is shown in FIGS. 13(a)-13(f). The process begins with a silicon substrate covered with a silicon dioxide layer as shown in FIG. 13(a). In other examples, instead of a silicon substrate covered with a silicon dioxide layer, an insulator, such as sapphire or quartz, may be used. Next, graphene is deposited onto the substrate FIG. 13(b). The graphene may be formed using, for example, CVD or exfoliation. In some cases, relatively large pieces (e.g., greater than 20 µm by 20 µm) of single-layer graphene may be used. Such graphene pieces could produce capacitances on the order of a few pF, which is high enough to allow characterization of LC circuits. In some examples, the graphene is single-layer and not bilayer or multi-layer, since each layer increases the density of states, increasing $C_Q$ and reducing the tuning range. For this reason, CVD graphene grown on Cu foils and transferred onto SiO$_2$, quartz, or sapphire substrates may be used. Because the CVD graphene growth technique is a self-limiting process, very large single-layer graphene sheets can be realized. The graphene may be patterned into the desired geometry using optical lithography and etching as shown in FIG. 13(c).

The process also includes depositing a high-κ gate dielectric and gate metal as shown in FIG. 13(d), patterning and etching the gate stack as shown in FIG. 13(e), and patterning and depositing contact electrodes as shown in FIG. 13(f). Electron-beam lithography may be used for patterning and etching the gate stack and contact electrodes, and feature sizes down to 20 nm are possible with comparable alignment tolerances. Results of the graphene physical characterization and back-gated FET measurements are shown in FIGS. 14(a)-14(d).

FIG. 14(a) is a contrast-enhanced optical micrograph of an example of a large piece of exfoliated single-layer graphene. FIG. 14(b) is an atomic force microscopy (AFM) image of an example single-layer graphene on a silicon oxide (SiO$_2$) substrate. FIG. 14(c) is a plot of Raman spectroscopy results from an example single-layer graphene piece. FIG. 14(d) is a plot of an example drain current versus gate voltage ($I_d$-$V_g$) characteristic of an example back-gated graphene field-effect transistor.

The ability to achieve low EOT, low leakage gate dielectrics would be beneficial for many device applications of graphene, including FETs for RF and digital applications. Various techniques may be used throughout the process, such as direct deposition of thin dielectrics and atomic-layer deposition, a technique that is highly useful for depositing few-nm dielectrics on silicon. An interfacial polymer or surface functionalization layer may be used prior to ALD. One example approach for gate dielectric deposition includes utilization of an inverted device structure, where the gate metal and dielectric are deposited first, followed by deposition of the graphene on top. This technique has the advantage that the ALD film does not have to be deposited onto the graphene directly, but rather onto the metal electrode. When using exfoliated graphene in the inverted design, the graphene is aligned to the gate electrode, and sufficiently large pieces are used to ensure a large capacitance can be achieved. Therefore, as an alternative, large-area CVD graphene is one example that may be used.

As can be seen in FIG. 8(d), described above, reducing the contact resistance may aid device performance. The contact resistance of metals to single-layer graphene may be optimized. In optimizing the contacts, varactors have a different set of constraints compared to conventional graphene FETs. In FETs, the conductivity is only modulated under the gate electrode, and so the contact resistance remains constant over the entire regime of device operation. However, in the varactor, the contact resistance could change as the sensing environment is changed. In the buried oxide sensing configuration shown in FIG. 3(a), trapped charge in insulator layer 14 will not only affect the conductance under gate 20, but also under contact electrodes 22 and 24. This change in the conductance could affect the contact resistance, particularly when the net carrier concentration is near zero. Fortunately, the sensitivity of the varactor performance to the contact resistance is greatest at high carrier concentrations; therefore, it may be acceptable for the device operation if the contact resistance increases with decreasing carrier concentration.

An additional advantage for the varactors compared to FETs is that they can operate using either electrons or holes as the dominant channel carriers, and so the contacts need to be optimized for one or the other carrier types, but not both. This is important, particularly since several chemical doping methods have been developed that provide high p-type doping, but fewer techniques have been developed to produce n-type doping. The sensing geometry may also be important for improving the contact resistance, and use of an inverted structure could be beneficial in reducing the dependence of the contact resistance on the sense charge.

A varactor having the buried oxide device geometry may be used as a radiation sensor. In the graphene varactor, the buried $SiO_2$ acts as a collection layer for radiation-induced charge where extremely-small size is essential. For example, a radiation sensor that utilizes a graphene varactor may be utilized for dosimeters in radiation cancer therapy, providing significant form-factor (e.g., size) advantages over current MEMS-based solutions. In some examples, the miniature dosimeter may provide real-time feedback in radiation dosimetry.

A graphene varactor could have substantial and immediate impact. The miniaturization of sensors is critical for numerous applications, particularly, in vivo sensing applications, where the ability to implant a sensor with minimal incision size is critical. Because a graphene varactor has orders-of-magnitude improvement in the capacitance per unit area compared to MEMS sensors, the graphene varactor has enormous potential for miniaturizing a variety of charge-based sensors.

Figure 15:
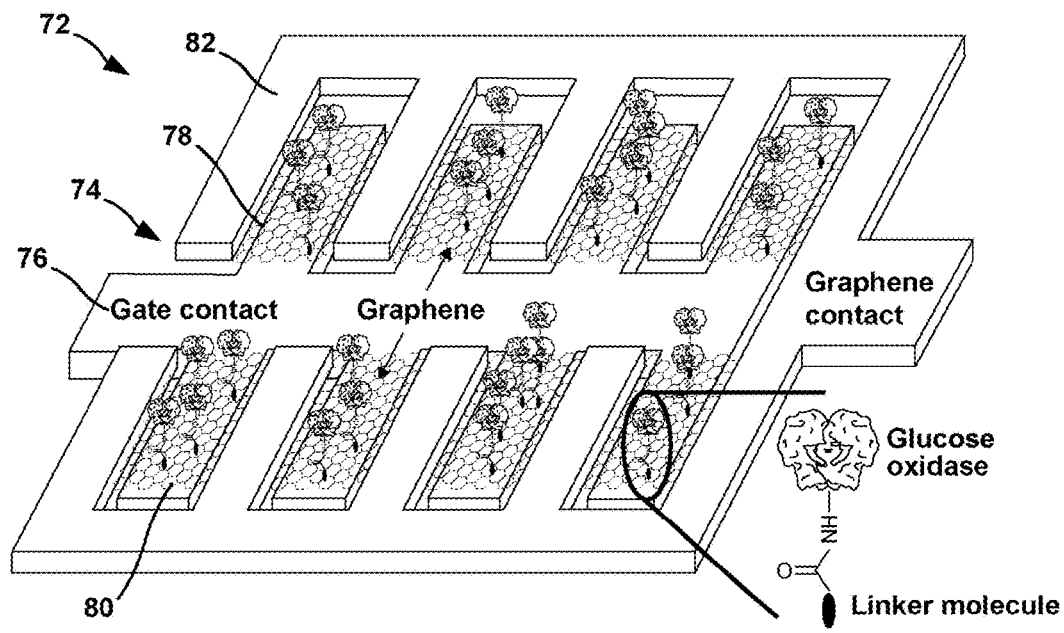
FIG. 15 is a conceptual diagram that illustrates an example glucose sensor that utilizes a graphene varactor.

FIG. 15 is a conceptual diagram that illustrates an example glucose sensor 72 that utilizes a graphene varactor 74. In the example shown in FIG. 15, graphene varactor 74 includes a structure similar to that shown and described with reference to FIGS. 4(a)-4(b). Graphene varactor 74 includes a buried gate electrode 76, a thin insulating dielectric layer (not shown in FIG. 15), sheets of single-layer graphene 78 and 80, and a metallization layer 82 to make electrical contact to the graphene sheets 78 and 80. Glucose sensor 72 also includes linker molecules, such as 1-pyrenebutanoic acid succinimidyl ester, attached to the exposed surface of graphene sheets 78 and 80. In some examples, the linker molecule may include a pyrene group that binds on one end to the surface of one of graphene sheets 78 or 80 through pi-pi interactions. The other end of the linker molecule may include a succinimidyl ester group that is attached to an enzyme, such as glucose oxidase.

Glucose oxidase catalyzes the oxidation of β-D-glucose ($C_6H_{12}O_6$) to D-glucono-1,5-lactone ($C_6H_{10}O_6$). The products of this oxidation reaction can reversibly change the electron concentration in the graphene sheets 78 and 80. The electron concentration change results in a shift of the capacitance of graphene varactor 74, which can be detected wirelessly when varactor 74 is incorporated in a passive LC resonator circuit, such as resonator 52 shown in FIG. 10(b).

Figure 16:
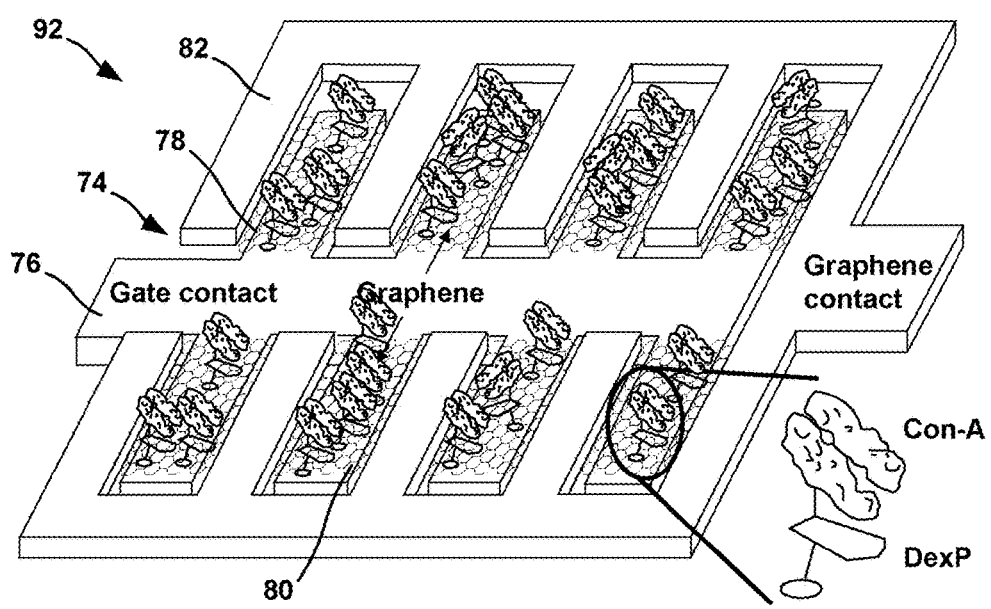
FIG. 16 is a conceptual diagram that illustrates another example glucose sensor that utilizes a graphene varactor.

FIG. 16 is a conceptual diagram that illustrates another example glucose sensor 92 that utilizes a graphene varactor 74. In the example shown in FIG. 16, graphene varactor 74 includes a structure similar to that shown and described with reference to FIGS. 4(a)-4(b). Graphene varactor 74 includes a buried gate electrode 76, a thin insulating dielectric layer (not shown in FIG. 16), sheets of single-layer graphene 78 and 80, and a metallization layer 82 to make electrical contact to the graphene sheets 78 and 80. Glucose sensor 72 also includes 1,2-epoxy-3-phenoxypropane-derivated dextran (DexP) attached to the exposed surface of graphene sheets 78 and 80. The DexP molecules can adsorb on the surface of graphene sheets 78 and 80 due to pi-pi interactions between the surface graphene sheets 78 and 80 and the DexP. On top of the DexP, Concanavalin A (ConA), a carbohydrate binding protein, is situated, where the ConA molecules are conjugated on the DexP.

ConA has a stronger affinity for glucose than for DexP. Because of this, in the presence of glucose, ConA molecules can desorb from the DexP. The change in the bonding configuration of the DexP is expected to change the electron concentration in the graphene due to electrostatic coupling between the DexP and the graphene. Through the quantum capacitance effect, this change in the carrier concentration can result in a shift of the capacitance of graphene varactor 74, and this shift can be detected wirelessly when the varactor 74 is incorporated in a passive LC resonator circuit, such as resonator 52 shown in FIG. 10(b).

Figure 17:
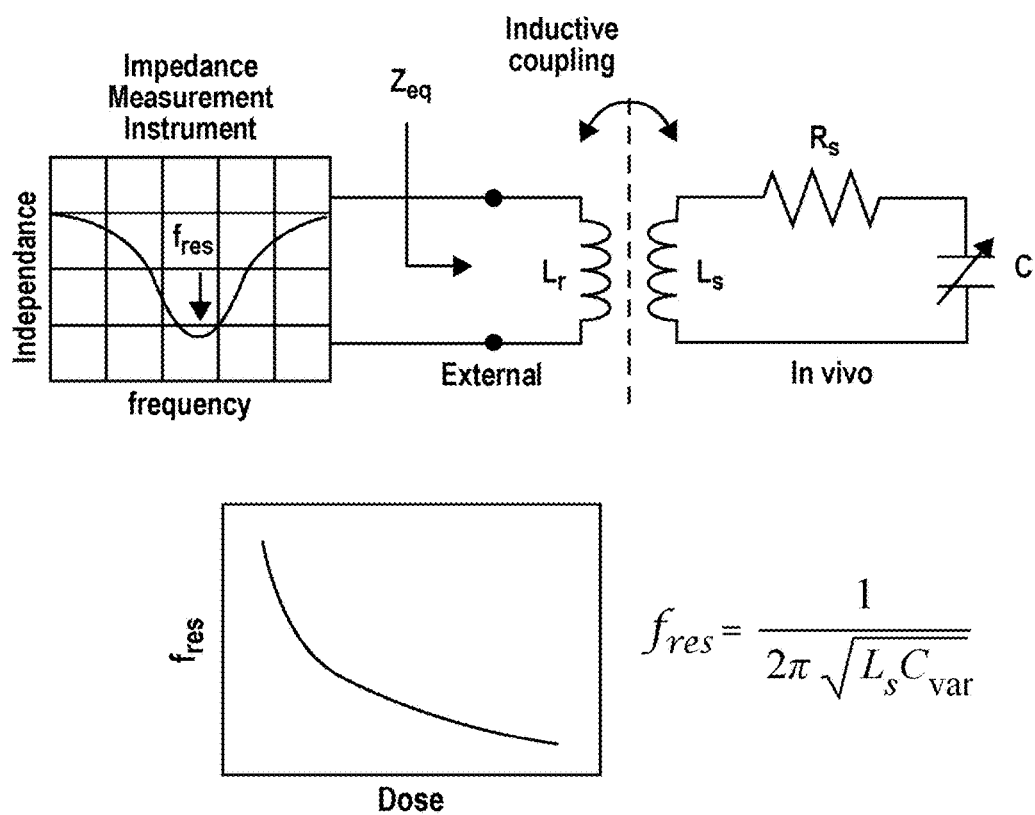
FIG. 17 illustrates an example wireless detection system that includes a graphene varactor.

FIG. 17 illustrates an example wireless detection system in which the varactor is connected to a first inductor $L_s$ of an LC oscillator circuit. Any sense charge collected by the varactor changes the capacitance of the varactor, which in turn, changes the resonant frequency of the LC oscillator circuit. Sample information (e.g., radiation dose or glucose concentration) can be determined using a second "external" inductor $L_r$, which is coupled to the first inductor through mutual magnetic field coupling (mutual inductance), via a "phase-dip" technique, which is shown in the FIG. 17. Other, more sophisticated, wireless detection schemes are also possible.

Various examples have been described. These and other examples are within the scope of the following claims.

The invention claimed is:

1. A sensor comprising:
a graphene quantum capacitance varactor comprising:
an insulator layer;
a dielectric layer;
a gate electrode between the insulator layer and the dielectric layer;
a graphene layer on the dielectric layer, wherein capacitance of the graphene layer changes in response to a sensed electrical charge collected proximate to the graphene layer upon exposure to a sample, and wherein the graphene layer comprises an exposed surface opposite the dielectric layer; and
at least one contact electrode on the graphene layer and making electrical contact with the graphene layer.

2. The sensor of claim 1, further comprising a readout circuit responsive to the capacitance of the graphene layer and configured to output a signal indicative of the electrical charge.

3. The sensor of claim 2, wherein the readout circuit comprises an inductor electrically connected to the graphene quantum capacitance varactor, wherein the inductor and the graphene quantum capacitance varactor form an LC oscillator circuit having a resonant frequency responsive to the electrical charge collected by the at least one graphene quantum capacitance varactor.

4. The sensor of claim 1, wherein the gate electrode is recessed in the insulator layer.

5. The sensor of claim 1, wherein the graphene quantum capacitance varactor further comprises a protective insulator formed on the exposed surface of the graphene layer.

6. The sensor of claim 1, further comprising:
at least one linker molecule attached to the exposed surface of the graphene layer or a protective insulator formed on the exposed surface of the graphene layer; and
an enzyme attached to the linker molecule.

7. The sensor of claim 6, wherein the linker molecule comprises 1-pyrenebutanoic acid succinimidyl ester and the enzyme comprises glucose oxidase.

8. The sensor of claim 1, further comprising:
1,2-epoxy-3-phenoxypropane-derivated dextran (DexP) attached to the exposed surface of the graphene layer or a protective insulator formed on the exposed surface of the graphene layer; and
Concanavalin A (ConA) conjugated on the DexP.

9. The sensor of claim 1, further comprising linker molecules attached to an exposed surface of the graphene layer.

10. The sensor of claim 1, further comprising glucose-sensitive molecules attached to the sensor proximate the graphene layer.

11. The sensor of claim 1, wherein the gate electrode is a multi-finger structure comprising at least two gate electrode fingers, the sensor further comprising a readout circuit configured to output a signal indicative of a change to the capacitance of the graphene layer.

12. The sensor of claim 11, wherein the graphene quantum capacitance varactor has an equivalent oxide thickness (EOT) of less than about 5 nanometers (nm).

13. The sensor of claim 11, wherein the graphene quantum capacitance varactor has a capacitance modulation ratio of greater than about 1.2.

14. The sensor of claim 11, further comprising linker molecules attached to an exposed surface of the graphene layer.

15. The sensor of claim 14, wherein the linker molecules attached to the exposed surface of the graphene layer comprise glucose-sensitive molecules.

16. The sensor of claim 11, wherein the readout circuit comprises an inductor electrically connected to the graphene quantum capacitance varactor, wherein the inductor and the graphene quantum capacitance varactor form an LC oscillator circuit having a resonant frequency responsive to the electrical charge collected by the graphene quantum capacitance varactor.

* * * * *